US005843706A

United States Patent [19]

Cobon et al.

[11] Patent Number: 5,843,706

[45] Date of Patent: Dec. 1, 1998

[54] VACCINES AGAINST ANIMAL PARASITIC NEMATODES

[75] Inventors: Gary Stewart Cobon, Frenchs Forest; Rosemary Ann Austen, East Gosford; Ian Joseph O'Donnell, Gardenvale; Maurice Joseph Frenkel, South Caulfield; William Peter Keith Kennedy, Willoughby; Keith William Savin, Caulfield South; Barry Maxwell Wagland, Carlingford, all of Australia

[73] Assignees: Biotechnology Australia Pty, Ltd., Roseville; Commonwealth Scientific and Industrial Organization, Campbell, both of Australia

[21] Appl. No.: 483,812

[22] Filed: Jun. 7, 1995

Related U.S. Application Data

[63] Continuation of Ser. No. 353,658, filed as PCT/AU88/00237, Jul. 6, 1988, abandoned.

[30] Foreign Application Priority Data

| | | | |
|---|---|---|---|
| Jul. 7, 1987 | [AU] | Australia | PI294D |
| Jul. 5, 1988 | [NZ] | New Zealand | 225295 |
| Jul. 6, 1988 | [CA] | Canada | 571319 |

[51] Int. Cl.$^6$ .......... C12N 15/00; C07H 21/04; A61K 39/00

[52] U.S. Cl. .......... 435/69.1; 435/69.7; 435/252.3; 435/320.1; 536/23.1; 536/23.4; 536/23.5; 536/23.7; 424/265.1; 424/184.1; 424/130.1; 530/300; 530/350; 530/387.1; 530/388.6

[58] Field of Search .......... 536/23.1, 23.6, 536/23.5, 23.7; 435/69.1, 252.3, 320.1, 69.7; 424/265.1, 184.1, 130.1; 530/300, 350, 387.1, 388.6

[56] References Cited

U.S. PATENT DOCUMENTS

| | | | |
|---|---|---|---|
| 4,670,384 | 6/1987 | Gamble et al. . | |
| 4,879,213 | 11/1989 | Fox et al. . | |
| 5,021,342 | 6/1991 | Green et al. | 435/91 |

FOREIGN PATENT DOCUMENTS

| | | |
|---|---|---|
| 247354 | 10/1963 | Australia . |
| 894603 | 4/1962 | United Kingdom . |
| 89-00401 | 6/1988 | WIPO . |
| 9003433 | 5/1990 | WIPO . |

OTHER PUBLICATIONS

Lazar et al Mol. Cell. Biol. 1988 vol. 8, No. 3, 1247–1252.

Burgess et al J. Cell. Biol. 1990 vol. 111, 2129–2138.

Siberstein et al., "Antigenes for *Trichinella spiralis* That Induce a Protective Response in the Mouse", J. Immunology, 132 pp. 898–904 (1984).

Hotez et al., "Isolation, Cloning and Expression of a Protease From Ancylostoma Hookworms", Journal of Cellular Biochemistry, UCLA Symposia on Molecular and Cellular Biology, Suppl. 10A, p. 132 (1986).

Hotez et al., "Isolation and Characterization of Proteolytic Enzyme From the Adult Hookworm *Ancylostoma caninum",* The Journal of Biological Chemistry, 260, pp. 7343–7348, (1985).

Laemmli, U.K. (1970), "Cleavage of structural proteins during the assembly of the head of bacteriophage T4", Nature 227 680–685.

Maryama et al. (1986), "Codon usage tabulated from the GenBank genetic sequence data", Nucleic Acids Research 14 r151–r197.

May, R.B. (1985), "Evolution of pesticide resistance" Nature 315 12–13.

Payne, J.W. (1973), "Polymerization of proteins with glutaraldehyde: soluble molecular weight markers" Biochem. J. 135 867–873.

Racusen, D. (1979), "Glycoprotein detection in polyacrylamide get with thymol and sulfuric acid", Analytical Biochemistry 99 474–476.

Rubin et al. (1983), "Two–dimensional polyacrylamide gel electrophoresis of membrane proteins" Methods in Enzymology 96 184–193.

Ruther, U. et al. (1983), "Easy identification of CDNA clones". EMBO Journal 2 1791–1794.

Sanger, R. et al. (1980), "Cloning in single bacteriophage as an aid to rapid DNA sequencing", J. Mol. Biol, 143 161–178.

Towbin, H. et al. (1979), "Electrophoretic transfer of proteins from polyacrylamide gels to nitrocellulose sheets: procedure and some applications", PNAS 76 4350–4353.

Wallace, R. B. et al. (1980), "Directed deletion of yeast transfer RNA intervening sequence", Science 209 1396–1400.

Yanisch–Perron, C. et al. (1985), "Improved M13 phage cloning vectors and host strains: nucleotide sequences of the M13mp18 and pUC19 vectors", Gene 33 103–119.

Vieira J., et al. (1982), "The puC plasmids, and M13mp17–derived system for insertion mutagenesis and sequencing with synthetic universal primers", Gene 19 259–268.

Reed, K.C. "Nucleic Acid Hybridizations with DNA Bound to Zeta–Probe Membrane", BIO–RAD Bulletin 1234.

Benton et al. (1977), "Screening Lanbda gt Recombinant clones by hybridization to single plagues in situ", Science 196: 180–182.

(List continued on next page.)

*Primary Examiner*—Paula K. Hutzell
*Assistant Examiner*—Khalid Masood
*Attorney, Agent, or Firm*—Foley & Lardner

[57] ABSTRACT

The invention disclosed relates to proteins derived from parasitic nematodes that confer protective immunity against infection by parasitic nematodes, to nucleotide sequences encoding those proteins, to recombinant molecules containing such sequences, to host cells transformed with such recombinant molecules and methods for the production of the nucleotide sequences, recombinant molecules and hosts. The invention also relates to vaccines comprising proteins of the invention together with suitable carriers or diluents and to antibodies raised against proteins of the invention.

26 Claims, No Drawings

OTHER PUBLICATIONS

Dineen, J.K. (1984), "Immunological control of helminthiases by genetic manipulation of host and parasite", Immunogenetic approaches to the control of endoparasites with particular reference to parasites of sheep (J.K. Dineen and P.M. Otteridge, eds.) CSIRO, Australia, pp. 1–9.

O'Donnell, I.J. (1973), "A search for a simple keratin fractionatin and peptide mapping of proteins for feather keratins", Aust. J. Biol. Sci. 26 401–413.

Hunke et al., J. Biol. Chem. 262: 17370–17373, 1987, Database search (1) only.

Hunke et al., Gene 45: 211–214, 1986.

Maniatis et al., "Molecular Cloning", A Laboratory Manual 1982, Cold Spring Harbor Chapter 6–10.

Selkirk et al., Parasitology 1986 91: 515–538.

Noble et al., Parasitology, 5th Ed. 1982.

Hanke et al., Database search, Gene: 45: 211–214, 1986.

D.B. Adams et al. (1984), "Basis for the development of vaccines for control of diseases produced by metazoan parasites", Rural Sciences 6 67–74.

Dineen et al., (1977), "The role of immunologically specific and non–specific components of resistance in cross–protection to intestinal nematodes", Journal for Parasitology 7 211–215.

Dineen and Wagland, (1982), "Immunoregulation of parasites in natural host–parasite system—with special reference to the gastrointestinal nematodes of sheep", Biology and Control of Endoparasites (L.E.A. Symons et al. eds.), Academic Press, pp. 297–323.

J.K. Dineen, (1984), "Immunological control of helminthiases by genetic manipulation of host and parasite", Immunologenetic approaches to the control of endoparasites with particular reference to parasites of sheep (J.K. Dineen et al., eds.) CSIRO, Australia, pp. 2–8.

A.P. Feinberg et al., (1984), "A technique for radiolabelling DNA restriction endonuclease fragments to high specific activity", Analytical Biochemistry 137 266–267.

M. Hattori et al., (1986), "Dideoxy sequencing method using denatured plasmid templates", Analytical Biochemistry 152 232–238.

J.G. Howe et al. (1981), "A sensitive immunoblotting method for measuring protein synthesis initiation factor levels in lysates of *Escherichia coli",* Journal of Biological Chemistry 256 12836–12839.

T.V. Huynh et al., (1985), "Construction and screening of cDNA libraries in lambda gt10 and lambda gt11", pp. 49–78, DNA Cloning vol. 1 (D.M. glover, ed.).

F.D.A. Johnson et al., (1984), "Improved technique utilizing non fat dry milk for analysis of proteins and nucleic acids transferred to nitrocellulose", Gene Anal. Tech. 1:3–8.

P. Kohler, (1986), "Progress in molecular parasitology", Eperientia 42 377–386.

N.M. McKern et al, (1985), "Primary structure of pilin protein for *Bacteroides nodosus* strain 216: comparison with the corresponding protein from strain 198", Journal of General Microbiology 131 1–6.

Munn et al., (1983), "Endotube brush border complexes dissected from the intestines of *Haemonchus contortus* and *Ancyclostoma caninum",* Parasitology 87 129–137.

J.T.M. Neilson, (1975), "Failure to vaccinate lambs against *Haemonchus contortus* with functional metabolic antigens identified by immunoelectrophoresis", Int. J. Parasitology 5 427–430.

Neilson et al., (1987), "Partial protection of lambs against *Haemonchus contortus* by vaccination with a fractionated preparation of the parasite", Veterinary Parasitology 23 211–221.

O'Donnell, (1973), "A search for a simple keratin fractionatin and peptide mapping of proteins from feather keratins", Aust J. Biol. Sci 6 401–413.

O'Donnell et al., (1985), "Attempts to probe the antigens and protective immunogens of *Trichostrongylus colubriformus* in immunoblots with sera from infected and hperimmune sheep and high and low responder guinea pigs", Int. J. Parasitology 15 129–136.

Rothwell et al., (1974), "Vaccination against the nematode *Trichostrongylus clubriforms* –1. Vaccination of guinea pigs and worm homogenates and soluble products released during in vitro maintenance", Int. Journal for Parasitology 4 293–299.

Rothwell et al., (1977), "Comparison of the kinetics of expulsion of *Trichostrongylus colibriformus* from previously uninfected, reinfected and vaccinated guinea pigs", J. Parasitology 63 761–762.

Rothwell, (1978), "Vaccination against the nematode *Trichostrongylus colubriformis* – III. Some observations on factors influencing immunity to infection in vaccinated guinea pigs", Int. J. for Parasitology 8 33–37.

Silberstein et al., (1985), "Effects on *Trichinella spiralis* of host response to purified antigens", Science 227 948–950.

Stearne et al., (1985), "The murine plasma cell antigen PC–1: purification and partial amino acid sequence", The Journal of Immunology 134 443–448.

Ulrich et al., "Isolation of the human insulin–like growth factor I gene using a single synthetic DNA probe", The EMBO J.

Nilsen et al., "Cloning and Characterization of a Potentially Protective Antigen Lymphatic Filariasis", Proc. Natl. Acad. Sci. (USA), 85 (10) 1988 Coden USA, pp. 3604–3607.

Munn et al., "Vaccination of Young Lambs By Means of a Protein Fraction Extracted From Adult *Haemonchus Contorus*", Parasitology, vol. 94 issued 1987, pp. 385–397.

Morgan et al., "Antigens Characterization of Adult *Wuchereria bancrofti* Filarial Nematodes", Parasotology, vol. 93, issued May 1986, pp. 559–569.

Fetterer et al., "*Ascaris suum*: Partial Isolation and Characterization of Hypodermis from Adult Female", Experimental Parasotology, vol. 63, issued Jan. 1987, pp. 312–318.

Kimura et al., "Troponin From Nematode: Purification and Characterization of Troponin for Ascaris Body Wal Muscle", Comp. Biochem. Physiol., vol. 88 B(2), issued 1987, pp. 399–407.

VACCINES AGAINST ANIMAL PARASITIC NEMATODES

This application is a continuation of Ser. No. 07/353,658, filed May 2, 1989, which is a national stage filing pursuant to 35 USC §371 of PCT/AU88/00239, filed Jul. 6, 1988.

TECHNICAL FIELD

The invention relates to the identification of proteins that confer protective immunity against infection by parasitic nematodes such as *Trichinella spiralis* or *Ancylostoma caninum* infections of man, *Strongylus vulgaris* infections of horses, *Trichostrongylus colubriformis* infections of sheep, *Haemonchus contortus* infections of sheep and goats, *Ostertagia ostertagi* infections of cattle, *Ascaris suum* or *Trichinella spiralis* infections of pigs, *Toxascaris leonina* or *Uncinaria stenocephala* infections of cats, *Ancylostoma caninum* or *Trichuris vulpis* infections of dogs, *Dirofilaria immitis* infections of dogs, infections of man by larvae of Toxocara spp, and infection by *Necator americanus, Ancylostoma duodenale, Ascaris lumbricoides, Trichuris trichiura, Enterobius vermicularus, Strongyloides stercorals* or *Wuchereria bancrofti.*

The invention further provides nucleotide sequences encoding these proteins or derivatives thereof as well as recombinant molecules containing such nucleotide sequences and host cells expressing these nucleotide sequences. The invention also provides methods for the production of the nucleotide sequences, recombinant molecules and hosts of the invention.

Additionally, the invention relates to vaccines conferring protective immunity against infection by parasitic nematodes such as *Trichinella spiralis* or *Ancylostoma caninum* infections of man, *Strongylus vulgaris* infections of horses, *Trichostrongylus colubriformis* infections of sheep, *Haemonchus contortus* infections of sheep or goats, *Ostertagia ostertagi* infections of cattle, *Ascaris suum* or *Trichinella spiralis* infections of pigs, *Toxascaris leonina* or *Uncinaria stenocephala* infections of cats, *Ancylostoma caninum* or *Trichuris vulpis* infections of dogs, *Dirofilaria immitis* infections of dogs and infections of man by larvae of Toxocara spp. and infection by *Necator americanus, Ancylostoma duodenale, Ascaris lumbricoides, Trichuris trichiura, Enterobius vermicularus, Strongyloides stercorals* or *Wuchereria bancrofti.*

BACKGROUND ART

Nematodes (nema—thread; oides—resembling), which are unsegmented roundworms with elongated, fusiform, or saclike bodies covered with cuticle, are virtually ubiquitous in nature, inhabiting soil, water and plants, and are importantly involved in a wide range of animal and plant parasitic diseases.

The roundworm parasites of mammals belong to the phylum Nematheimunthes. The roundworms include the hookworm (e.g. *Necator americanus* and *Ancylostoma duodenale*), roundworm (e.g. the common roundworm *Ascaris lumbricoides*), whipworm (e.g. *Trichuris trichiura*), and the pinworm or threadworm (e.g. *Enterobius vermicularus*), as well as *Strongyloides stercorals, Trichinella spiralis* (infection in man and pigs), and the filarial worm *Wuchereria bancrofti.* Other important roundworm parasites include *Ancylostoma caninum* (infections of man), *Strongylus vulgaris* (infections of horses), *Trichostrongylus colubriformis* (infections of sheep), *Haemonchus contortus* (infections of sheep and goats), *Ostertagia ostertagi* (infections of cattle), *Ascaris suum, Toxascaris leonia* or *Uncinaria stenocephala* (infections of dogs), Toxocara spp (circulatory infections of man) and *Dirofilaria immitis* (circulatory infections of cats and dogs).

Even when symptom-free, parasitic worm infections are harmful to the host animal for a number of reasons; e.g. they deprive the host of food, injure organs or obstruct ducts, may elaborate substances toxic to the host, and provide a port of entry for other organisms. In other cases, the host may be a species raised for food and the parasite may be transmitted upon eating to infect the ingesting animal. It is highly desirable to eliminate such parasites as soon as they have been discovered.

More commonly, such infections are not symptom-free. Helminth infections of mammals, particularly by parasitic nematodes, are a source of great economic loss, especially of livestock and pets, e.g. sheep, cattle, horses, pigs, goats, dogs, cats, and birds, especially poultry (see CSIRO/BAE Report—"Socio-economic Developments and Trends in the Agricultural Sector: Implications for Future Research). These animals must be regularly treated with antihelminthic chemicals in order to keep such infections under control, or else the disease may result in anemia, diarrhea, dehydration, loss of appetite, and even death.

The only currently available means for controlling helminth infections is with the use of antihelminthic chemicals, but these are only effective against resident worms present at the time of treatment. Therefore, treatment must be continuous since the animals are constantly exposed to infection; e.g. antihelminthic treatment with diethylcarbamazine is required every day or every other day most of the year to control *Dirofilaria immitis* or the dog heartworm. This is an expensive and labor intensive procedure. Due to the widespread use of anthelminthic chemicals, the worms may develop resistance and so new and more potent classes of chemicals must be developed. An alternative approach is clearly desirable.

The development of a vaccine against parasitic nematodes would overcome many of the drawbacks inherent with chemical treatment for the prevention and curing of helminthic infections. The protection would certainly last longer, only the vaccinated animal would be affected, and the problems of toxicity and persistence of residues would be minimized or avoided. Accordingly, there have been several attempts reported in the prior art to develop such vaccines using parasitic nematodes; unfortunately, they have met with limited success and factors such as material availability and vaccine stability have precluded their large scale use.

One such application described by J. K. Dineen et al., (1977) involves the use of irradiated larval vaccines. As with other such attempts, the utility of this method is restricted by the requirement to maintain viable nematodes for prolonged periods.

The failure of killed vaccine preparations to afford good antihelminthic protection has been thought to be due to a number of factors. For example, it has been considered by J. T. M. Neilson, (1975) that parasitic nematodes may have evolved mechanisms by which they can secrete products which immunosuppress or immunomodulate the host's immune system, thereby both preventing the development of an effective immune response and rendering the host susceptible to other infections. It is believed by Dineen and Wagland (1982), that immunosuppressants or immunodulators may be present in the crude preparations of parasitic nematodes which are used in the killed vaccines. A second problem suggested by this review article is that parasitic nematodes may have altered their antigen profile to one which resembles that of the host so that, in a natural infection, vigorous immunological reactions are not provoked by protective parasitic antigens. Such a phenomenon would also occur following vaccination with impure preparations of killed nematodes or extracts thereof.

Recent advances in biotechnology and in particular recombinant DNA technology, realistically offer the opportunity to produce commercially-viable vaccines against a range of economically-important parasites of man and domestic animals. Although it has been demonstrated (e.g. O'Donnell et al 1985) that many parasite proteins are recognised by host animals during parasitic infection, many of the immune responses will have no functional significance in terms of resistance to re-infection. The major step is to identify, from the many thousands of proteins present in the parasitic organism, the individual proteins that can induce immune responses in the host animal that protect it from re-infection. Once identified, recombinant DNA technology could be used to construct microorganisms which synthesize those proteins or portions or the proteins containing protective epitopes and use the products synthesized by the recombinant organism in vaccines to protect animals from infection with the parasites. This approach would overcome many of the problems proposed to account for the lack of efficacy of killed vaccines using crude parasite preparations discussed above. For example, the vaccines produced by recombinant DNA techniques would not contain immunosuppressants or immunomodulators which may be found in crude extracts of parasitic nematode species.

The CSIRO/BAE working paper "Socio-economic Developments and Trends in the Agricultural Sector: Implications for the Future Research" cited intestinal parasites as one of the three most urgent health problems in the Australian sheep industry and indicated that the development of vaccines holds great promise for better control of these infections.

*Trichostrongylus colubriformis* and *Haemonchus contortus* are two of the most important parasites of sheep. Several attempts have been made to vaccinate animals against infection with these species of parasite (see Adams and Cobon for Review).

For example, Rothwell and co-workers (1974, 1977, 1978) have done much work to show that the whole homogenate from 4th stage larvae of *T. colubriformis* caused accelerated expulsion of the worms from outbred guinea pigs, a laboratory model for sheep. Sub-fractions of this whole homogenate isolated by electrophoresis in polyacrylamide gels containing sodium dodecyl sulphate (SDS-PAGE) were later also shown to cause this accelerated expulsion (O'Donnell et al 1985). It has recently been reported that a high molecular weight fraction obtained from a somatic extract of *H. contortus* and excretions and secretions of larvae isolated during in vitro development could be used in a vaccine and resulted in a 59% reduction in the adult worm numbers compared with controls (Neilson and Van de Walle, 1987). Silverman makes similar claims in UK Patent No. 894,603 and Australian patent 247 354.

However in all of these reports, crude extracts have been used and no defined antigen or individual component of the extracts have been identified as being responsible for protection. The only nematode-host system where defined-antigens have proven host-protective to date is the *Trichinella spiralis*-mouse system studied by Despommier and colleagues (see Silverstein and Despommier 1985). Two antigens of molecular weights 48 kD and 50–55 kD have given host-protection of 68% and 39% respectively. In addition, it has been claimed (Munn and Greenwood, 1987) that a molecule referred to as contortin isolated from *H. contortus* can be used in a vaccine to reduce parasitism in sheep. However this material is not characterised at the molecular level and the means by which the fraction is prepared are such that it is highly likely that the preparation is very impure and contains many components. It has not been demonstrated which component is responsible for the marginal effects observed.

DESCRIPTION OF THE INVENTION

In the present invention, a molecule termed 41 kD is described which is isolated from *T. colubriformis.* When prepared in a non-native form, this molecule gives 43–51% protection to guinea pigs from infection by *T. colubriformis.* The gene coding for the 41 kD protein has been cloned from *T. colubriformis* and the closely related gene from *H. contortus* has also been cloned. Hybridisation studies and DNA sequence analysis of the two genes show that they are closely related. A polypeptide produced by recombinant organisms containing DNA sequences from *T. colubriformis* is capable of giving protection to guinea pigs against parasitism by *T. colubriformis.* In addition, the polypeptide produced from recombinant organisms containing DNA sequences from *H. contortus* is capable of giving protection to sheep against *H. contortus* infection and is also capable of giving protection to guinea pigs against *T. colubriformis* infection. Thus it can be confidently predicted that protection can be obtained in other animal species against a range of parasitic nematode species by vaccination with the recombinant proteins decribed in this invention or by proteins produced by recombinant DNA technology using related gene products from those other parasite species. The protein and DNA sequence analysis indicates that the proteins are closely related and are expected to be present in all other related forms of parasitic nematode species. By analogy the invention is extended to cover all major animal nematode parasites.

To describe the invention in more detail, third stage larvae of *T. colubriformis* were extensively washed with phosphate buffered saline (PBS) and then extracted with PBS buffer containing sodium deoxycholate (PBS-DOC). The PBS-DOC extract was found to contain only a few major protein bands. These proteins have now been isolated and their ability to cause accelerated expulsion of *T. colubriformis* from guinea pigs examined. It has been demonstrated that one of the proteins, referred to as the 41 kD protein elicits immunity to *T. colubriformis* infection following intraperitoneal injection.

The 41 kD protein has been purified from third stage larvae of *T. colubriformis* digested with *Armillaria mellea* protease, the peptide fragments resolved and partial amino acid sequences of these peptides determined. Oligonucleotide sequences suitable for hybridization probes have been designed and used to identify recombinant bacterial cells containing the gene coding for the *T. colubriformis* 41 kD protein. The DNA sequence of this gene has been determined. Recombinant organisms have been constructed which synthesize portions of the *T. colubriformis* 41 kD protein and the recombinant fusion protein isolated from the bacterial cells when used to vaccinate guinea pigs has been shown to cause accelerated rejection of *T. colubriformis* challenge infections.

Using DNA coding for the 41 kD protein of *T. colubriformis* as a hybridization probe, the presence of a gene encoding a related antigen in a cDNA library constructed from mRNA extracted from young adult *H. contortus* has been identified. The protein produced from this gene is recognised by antiserum raised again the *T. colubriformis* 41 kD protein.

The *H. contortus* DNA sequence has been cloned and bacteria have been constructed to express this protein. The protein purified from these bacteria has been used to vaccinate sheep. These sheep were subsequently challenged with *H. contortus* and the animals have been shown to be significantly protected from parasitism. In addition, the protein purified from bacteria expressing the *H. contortus* 41 kD peptide was used to vaccinate guinea pigs, which were subsequently infected with *T. colubriformis* and shown to be significantly protected from parasitism. These experiments demonstrate that the approaches used to clone, and express the *T. colubriformis* and *H. contortus* antigens are also applicable to providing vaccines against other species of parasitic nematodes such as *Trichinella spiralis, Ancylostoma caninum, Strongylus vulgaris, Ostertagia ostertagi, Ascaris suum, Trichinella spiralis, Toxascaris leonina, Uncinaria stenocephala, Ancylostoma caninum, Trichuris vulpis, Dirofilaria immitis,* larvae of Toxocara spp. *Necator americanus, Ancylostoma duodenale, Ascaris lumbricoides, Trichuris trichiura, Enterobius vermicularus, Strongyloides stercorals* or *Wuchereria bancrofti.*

In a first embodiment the invention provides a protein derived from a parasitic nematode species and capable of conferring protective immunity against infection of a host by a parasitic nematode species wherein said protein has an approximate molecular weight of 41 kD, as estimated by SDS-PAGE, or all, part, an analogue, homologue or derivative or combination thereof of said protein which is capable of conferring protective immunity against infection of a host by a parasitic nematode.

Preferably said parasitic nematode is *Trichinella spiralis, Ancylostoma caninum, Strongylus vulgaris, Ostertagia ostertagi, Ascaris suum, Trichinella spiralis, Toxascaris leonina, Uncinaria stenocephala, Ancylostoma caninum, Trichuris vulpis, Dirofilaria immitis,* larvae of Toxocara spp, *T colubriformis, H contortus, Necator americanus, Ancylostoma duodenale, Ascaris lumbricoides, Trichuris trichiura, Enterobius vermicularus, Strongyloides stercorals* or *Wuchereria bancrofti.*

Preferably said protein is derived from *T colubriformis* or *H contortus.*

A particularly preferred protein of the invention is a protein having the amino sequence depicted in Table 3 or Table 8 or all, part, an analogue, homologue or derivative or combination thereof capable of conferring protective immunity against infection by a parasitic nematode.

In a further embodiment the invention provides a first nucleotide sequence encoding amino acid sequences of all, part, analogues, homologues, derivatives or combinations thereof of a protein capable of providing immunity to infection by a pathogenic nematode, a nucleotide sequence which hybridizes to said first nucleotide sequence, or a nucleotide sequence related by mutation including single and multiple base substitutions, insertions, and deletions to said first nucleotide sequence.

Preferred nucleotide sequences of the invention include those encoding the amino acid sequences depicted in Tables 1, 2, 3, 7 and 8. Particularly preferred DNA sequences of the invention are described in Tables 3, 7 and 8.

Preferred sequences in the invention are those encoding polypeptides corresponding to a 41 kD antigen. The DNA sequences embraced by the present invention can be prepared for example from *T. colubriformis* or *H. contortus* cells by extracting total DNA therefrom and isolating the sequences by standard techniques. Alternatively, the DNA may be prepared in vitro, synthetically or biosynthetically such as by the use of an mRNA template.

Also within the scope of the present invention is a process for selecting a DNA or RNA sequence coding for all, part, analogues, homologues, derivatives or combinations thereof of a protein according to the invention which process comprises providing one or more DNA or RNA sequences and determining which of said sequences hybridizes with a DNA or RNA sequence known to code for all, part, analogues, homologues, derivatives or combinations thereof of polypeptides having such an activity or providing an antiserum to said protein or parts thereof and identifying host-vector combinations that express said protein.

The above sequence may be from natural sources, may be RNA sequences, synthetic sequences, DNA sequences from recombinant DNA molecules or combinations of such sequences.

In a preferred form of the present invention, the process used to identify and characterize DNA coding for at least a portion of the protein involves the extraction of mRNA species from cells producing the protein, their conversion to double stranded DNA (cDNA) and the insertion of these into an autonomously replicating factor, such as a plasmid. This is followed by transformation of a host cell such as a bacterial strain with the factor and screening of the library produced with synthetic DNA probes which are complementary to the protein encoding mRNA and DNA sequences in order to detect those clones which contain DNA coding for the protein as opposed to any other cell proteinaceous components.

In a further embodiment the invention provides recombinant DNA molecules characterized by a DNA insert comprising a first DNA sequence which codes for amino acid sequences of all, part, analogues, homologues, derivatives or combinations thereof of a protein according to the invention, or a DNA sequence which hybridizes with said first sequence, said sequences being derived from whatever source including natural, synthetic, biosynthetic, or semi-synthetic sources and which sequences include those related by mutation, single or muliple base substitutions, deletions, insertions and inversions and including sequences which code for all, part, analogues, homologues, derivatives or combination thereof of a protein according to the invention, and vector DNA. Preferred recombinant DNA molecules of the invention include an expression control sequence operatively linked to said DNA insert. In one preferred form of the invention, said DNA insert is operatively linked to the β-galactosidase gene of *E. coli.* Other preferred control systems include those of the tryptophan (trp operon), the leftward promoter of bacteriophage lambda ($P_L$) and hybrid promoter such as tac or viral promoters such as those of the long terminal repeat of Moloney leukaemia virus. A preferred recombinant DNA molecule of the present invention is a plasmid which contains a DNA insert as described above. Suitable plasmid vectors include the plasmids pUR290 and pUC18 and derivatives thereof. Preferred plasmids of the invention will be described in detail hereinafter and include pBTA593, pBTA597, pBTA598, pBTA702 & pBTA 704.

Alternatively, said recombinant DNA molecules may comprise said DNA insert linked to DNA of a suitable bacteriophage such as bacteriophage lambda or a derivative thereof.

The invention also provides a fused gene comprising a promoter, a translation start signal and a DNA sequence which is a DNA sequence according to the invention.

Also embraced within the present invention is a process for the manufacture of a recombinant DNA molecule which process comprises providing a DNA insert comprising a first DNA sequence which is a DNA sequence according to the invention and introducing said DNA insert into a cloning vector.

Preferably said DNA insert is introduced into the cloning vehicle in correct spacing and correct reading frame with an expression control sequence.

In a further embodiment of the present invention there is provided a host transformed with at least one recombinant DNA molecule of the present invention and capable of expressing all, part, analogues, homologues, derivatives or combinations thereof of a protein according to the invention or a polypeptide having similar immunological or biological activity to said protective antigen. Suitable hosts include bacterial cells, yeasts, other fungi, vertebrate cells or insert cells, plant cells, human cells, human tissue cells or whole eukaryotic organisms. Suitable bacterial hosts include *E. coli* and other enteric organisms, Pseudomonas and Bacillus species. Preferred host cultures are identified as *E. coli* K12 derivatives, in particular JM109 and Y1090.

Particularly preferred transformant strains according to the invention are *E coli* K-12 strains designated BTA 1621, BTA 1637, BTA 1638 and BTA 1684 and transformed with pBTA593, pBTA597, pBTA598 and pBTA702 respectively which were deposited with the American Type Culture Collection at 12301 Parklawn Drive Rockville, Md. 20852 USA on 17 Jun. 1987 and 28 Jun. 1988 for BTA 1684 and received accession numbers ATCC67438, ATCC67439, ATCC67440 and ATCC67738 respectively.

Also included within the scope of the present invention is a process for transforming a host which process comprises: providing a host and introducing into said host a recombinant DNA molecule of the present invention in correct reading frame.

The invention further provides expression products of the transformed host of the present invention which products comprise all, part, analogues, homologues, derivatives or combinations thereof of a protein according to the invention. Preferably these expression products are provided in substantially pure form.

In a preferred embodiment of the present invention the expression products comprise a first polypeptide sequence homologous to the host and a second polypeptide sequence which is the amino acid sequence coding for all, part, analogues, homologues, derivatives or combinations thereof of a protein according to the invention.

In a preferred embodiment of the present invention the first amino acid sequence is part or all of β-galactosidase and the host cell is *E. coli.*

In a further preferred embodiment of the invention the first sequence is the $NH_2$-terminal sequence of the expression product.

In a further embodiment of the present invention there is provided a process for the biosynthesis of a polypeptide which comprises all, part, analogues, homologues, derivatives or combinations thereof of a protein according to the invention which process comprises:

transforming a host with a recombinant DNA molecule of the present invention so that the host is capable of expressing a proteinaceous product which includes a polypeptide which is all, part, analogues, homologues, derivatives or combinations thereof of a protein according to the invention; culturing said host to obtain said expression; and collecting said polypeptide.

In a further embodiment the invention provides a vaccine comprising one or more expressed products or proteins of the invention together with a pharamaceutically acceptable carrier or diluent. Preferred vaccines include those suitable for oral administration or in injectable form and preferably include a pharmaceutically acceptable adjuvant.

In a further form the invention embraces antibody preparations prepared as a result of immunological challenge to a host by administration of one or more expression products, proteins or vaccines of the present invention. Such antibody preparations include polyclonal and monoclonal antibodies preparations.

The invention also includes within its scope the epitope or the epitopes on the protein which are responsible for the protective immune response. These epitopes may be created artificially by the synthetic production of oligopeptides which contain sequences of portions of the protein which can be predicted from the results of immunochemical tests on fragments of the protein produced in bacteria or generated as a result of chemical or enzymatic cleavage of the native of recombinant peptides.

The invention also relates to antibodies generated against those epitopes and to antibodies generated against the variable region of those first antibodies, so called anti-idiotype antibodies, which mimic the protective epitopes of the protein and may be used as effective vaccines in either passive protection of animals (idiotypes) or active immunization of animals (anti-idiotypes) and thereby result in effective protection.

BEST METHOD OF CARRYING OUT THE INVENTION

The invention is further described with reference to the following Examples. It is to be understood that other methodologies analogous to those described below would be apparent to persons skilled in the art and these lie within the scope of the invention described.

EXAMPLE 1

Preparation of Extracts

Parasitological Techniques

Third stage *T. colubriformis* larvae were obtained from culturing sheep faeces and Bearmanizing. They were kept in phosphate-buffered saline PBS (10 mM sodium phosphate, 150 mM sodium chloride, pH 7.4) at 4° C.

Extraction of *T. colubriformis*

2.0–2.5 g (centrifuged weight) of *T. colubriformis* third stage larvae were extracted 4 times each with 2.0 ml PBS plus 3.5 ml water. The buffer used in the first extraction contained in addition 1 mM phenylmethylsulphonyl fluoride, 0.2 mM p-chloromercuribenzoate, 5 mM ethylenediaminetetraacetate (EDTA) while the buffer used in the fourth extraction contained deoxyribonuclease (1 μg/1 ml). These extractions were followed by two extractions with PBS containing 1% sodium deoxycholate [PBS-DOC] and 1 μg/ml of deoxyribonuclease. Extractions were performed using a motor-driven ground-glass Potter-Elvejhem homogenizer. During the PBS-DOC extractions, the samples were additionally treated for three one minute intervals in ice, with a Mullard ultrasonic disintegrator type 7685/2 at approximately 60 watts power. For gel electrophoresis (O'Donnell et al 1985) 20 μl of each centrifuged extract was dried and then heated for 3 min at 100° C. with 15 μl sample buffer (Laemmli 1970). The PBS-DOC extract was centrifuged at 100,000 g for 1 hr before use and the pellet was discarded.

SDS-PAGE patterns of successive PBS extractions of *T. colubriformis* third stage larvae followed by a PBS-DOC extract indicate that. There are 4 major protein bands in the PBS-DOC extract which have been called 200 kD, 93 kD, 43 kD and 41 kD respectively. The 41 kD and 43 kD protein bands could be extracted using PBS without 1% DOC if the ultrasonic disintegrator was used but the 93 kD and 200 kD could not be efficiently extracted. The limited number of protein bands in the PBS-DOC extract contrasts with the multitude in the PBS extract. The 41 kD and 43 kD proteins could be efficiently extracted without the use of the ultrasonic disintegrator, with PBS—1% DOC but not with PBS—0.1% DOC. Ultrasonic disintegration gave a substantial increase in yield of proteins. If the deoxyribonuclease treatment was not performed, the PBS-DOC extract was very viscous due to the presence of DNA even after using the ultrasonic disintegrator.

The purified 41 kD protein was reduced and carboxy methylated in 8M urea at pH 10.5 according to the procedure described by O'Donnell (1973). The protein was then digested with *Armillaria mellea* protease for 16 hrs at 37° C. in 50 mM ammonium hydrogen carbonate at a pH of approximately 8.0 and using an enzyme:protein ratio of 1:50. The reaction mixture was then dried on a Savant Speed Vac Concentrator.

Oligopeptides resulting from protease digests of 41 kD were separated by HPLC using a Vydac C18 column and initial and final buffers consisting of 0.1% trifluoroacetic acid and 0.1% trifluoroacetic acid in 70% acetonitrile respectively.

Peptides isolated from the HPLC separation were sequenced manually using the procedure of McKern et al (1985) or automatically using a gas phase sequencer. The PTH amino acids were identified by HPLC.

Some of the amino acid sequences of HPLC-isolated peptides from an *A. mellea* digest of reduced and carboxymethylated 41 kD are presented in Table 1.

TABLE 1

Some amino acid sequences obtained from peptides produced following digestion of the *T. colubriformis* 41kD protein with *Armillaria mella* protease.

| | |
|---|---|
| 1. | LYS VAL MET GLU ASN ARG SER PHE GLN ASP GLU GLU ARG |
| 2. | LYS MET MET GLN THR GLU ASN ASP LEU |
| 3. | LYS ALA ILE SER GLU GLU LEU ASP SER ARG PHE GLN GLU LEU |
| 4. | LYS GLU VAL ASP ARG LEU GLU ASP GLU LEU VAL HIS |
| 5. | LYS TYR ASP GLU VAL ALA ARG |
| 6. | LYS SER LEU GLU VAL SER GLU GLU LYS ALA LEU GLN ARG GLU |
| 7. | LYS LEU GLU ARG VAL |

No end group could be found on the undigested 41kD protein by the gas phase sequencer and it must therefore be assumed that it is blocked.

EXAMPLE 2

Protein Analysis

Two-dimensional Fractionation of the PBS-DOC Extract

The procedure of Rubin and Leonardi (1983) was followed using Biolytes (Bio-Rad) for isoelectric focussing in the first dimension in 3 mm disc gels and Laemmli gels 1.5 mm thick and containing 10% polyacrylamide in the second dimension. The proteins were visualised with cold potassium chloride and the 41 kD protein was electro eluted and precipitated with cold methanol as described (Stearne et al 1985). This material was used for vaccination studies and for endoproteinase digestion.

Electrophoretic transfer from one- or two-dimensional gels to nitrocellulose (Bio-Rad) was performed in the standard manner. The nitrocellulose was then treated and probed with the various anti-sera by the procedure of Howe and Hershey (1981). Complexes were finally made visible by the reaction of bound antibodies with horseradish peroxidase conjugated to goat anti-rabbit IgG (Bio-Rad) followed by 4-chloro-1-napthol and $H_2O_2$.

Antisera from a rabbit immunised with 41 kD protein shows on immunoblots that the 41 kD protein exists in the 3rd and 4th larval stages as well as in the adults. The presence of carbohydrate was estimated in each component of the PBS-DOC extract following electroelution by assaying for the presence of glucosamine or galactosamine in acid hydrolysates and by the staining of gels using the method of Racusen (1979). Analyses showed no detectable carbohydrates in the 41 kD protein.

EXAMPLE 3

Identification and Characterization of the cDNA Clone Corresponding to the 41 kD Protein of *T. colibriformis*

I. Construction of cDNA Library

Messenger RNA was isolated from fourth stage larvae of *T. colubriformis* by grinding the larvae in a buffer containing 6M guanidine hydrochloride, 0.2M sodium acetate and 50 mM β-mercaptoethanol, followed by precipitation with ethanol and fractionation on an oligo(dT)-cellulose column. The mRNA was used as the template for synthesis of double-stranded cDNA using the Amersham ribonulease H/DNA polymerase I kit (Amersham cDNA synthesis system, #RPN.1256) as recommended by the manufacturers. Following the addition of EcoRI linkers, the double-stranded cDNA was ligated to lambda gtll and packaged into viable bacteriophage which were used to infect Y1090 cells, essentially as described by Huynh et al (1985). Using the above methods, a cDNA library was established consisting of $2\times10^5$ independent recombinants. The library was amplified and aliquots were screened using a synthetic oligonucleotide probe and duplicate filter lifts as described by Wallace et al (1985) and Benton and Davis (1977).

II Hybridization Probe

The 23-mer oligonucleotide sequence used to screen the library was based on a peptide sequence obtained from amino acid sequence 2 (Table 1) of the 41 kD protein.

| | | |
|---|---|---|
| Peptide | | LYS.MET.MET.GLN.THR.GLU.ASN.ASP. |
| Oligonucleotide | 5' | AAA ATG ATG CAA ACT GAA AAT GA |
| nucleotide | | G G C G C |
| Reverse Complement | 5' | TC ATT TTC AGT TTG CAT CAT TTT |
| | | G C G C C |

The reverse complement sequence was synthesised and used for the screening.

(The codons used for threonine codons are based on the preferred codon usage of *E. elegans:* Maruyama, et al 1986)

Approximately $2\times10^5$ recombinant bacteriophage were screened and 43 positives were detected.

III. DNA Sequencing

One of the selected clones, lambda gtll-4-41-6, contained a 700 bp insert which could be resected with EcoRI and subcloned into M13mp digested with the same enzyme. The DNA sequence of the subcloned insert was determined using the method of Sanger et al (1980) (Table 2).

A comparison of the sequence obtained with those in protein data banks shows that the 41 kD protein has homology with the amino sequences of tropomyosin from a variety of organisms e.g. the homology with rabbit was approximately 70%.

TABLE 2

DNA sequence of the Eco R1 cDNA fragment contained in plasmid pBTA 593 in clone BTA 1621 and the translated amino acid sequence coding for part of the 41kD protein of *T. colubriformis.*

| | | | | | | | | | | | | | | | | | | |
|---|---|---|---|---|---|---|---|---|---|---|---|---|---|---|---|---|---|---|
| | | | 10 * | | | 20 * | | | 30 * | | | | 40 * | | | 50 * | | |
| AAG | AAG | AAG | ATG | CAG | GCG | ATG | AAG | ATC | GAG | AAG | GAC | AAT | GCT | CTC | GAT | CGA | GGC | GAT |
| K | K | K | M | Q | A | M | K | I | E | K | D | N | A | L | D | R | A | D |
| 60 * | | | | 70 * | | | 80 * | | | 90 * | | | | 100 * | | | 110 * | |
| GCC | GCC | GAA | GAG | AAA | GTC | CGT | CAA | ATT | ACC | GAA | AAG | TTG | GAG | CGA | GTT | GAA | GAA | GAG |
| A | A | E | E | K | V | R | Q | I | T | E | K | L | E | R | V | E | E | E |
| | 120 * | | | | 130 * | | | 140 * | | | 150 * | | | | 160 * | | | 170 * |
| CTC | CGT | GAC | ACA | CAA | AAG | AAA | ATG | ATG | CAA | ACA | GAA | AAC | GAT | TTG | GAC | AAG | GCT | CAG |
| L | R | D | T | Q | K | K | M | M | Q | T | E | N | D | L | D | K | A | Q |
| | | 180 * | | | | 190 * | | | 200 * | | | 210 * | | | | 220 * | | |
| GAA | GAT | TTG | GCT | GCA | GCC | ACC | AGC | CAG | TTG | GAA | GAG | AAA | GAG | AAG | AAA | GTG | CAA | GAG |
| E | D | L | A | A | A | T | S | Q | L | E | E | K | E | K | K | V | Q | E |
| 230 * | | | 240 * | | | | 250 * | | | 260 * | | | 270 * | | | | 280 * | |
| GCT | GAG | GCA | GAG | GTA | GCT | GCC | CTG | AAC | CGT | CGC | ATG | ACT | CTT | CTC | GAA | GAA | GAG | CTT |
| A | E | A | E | V | A | A | L | N | R | R | M | T | L | L | E | E | E | L |
| | 290 * | | | 300 * | | | | 310 * | | | 320 * | | | 330 * | | | | 340 * |
| GAA | CGT | GCT | GAA | GAA | CGT | TTG | AAG | ATC | GCC | ACT | GAA | AAA | CTC | GAA | GAG | GCC | ACT | CAC |
| E | R | A | E | E | R | L | K | I | A | T | E | K | L | E | E | A | T | H |
| | | 350 * | | | 360 * | | | | 370 * | | | 380 * | | | 390 * | | | |
| AAT | GTC | GAC | GAG | TCC | GAG | CGT | GTA | CGC | AAA | GTG | ATG | GAG | AAC | GGC | TCA | TTC | CAA | GAT |
| N | V | D | E | S | E | R | V | R | K | V | M | E | N | G | S | F | Q | D |
| 400 * | | | 410 * | | | 420 * | | | | 430 * | | | 440 * | | | 450 * | | |
| GAG | GAG | CGT | GCC | AAC | ACG | ATT | GAA | GCT | CAA | CTG | AAG | GAA | GCC | CAG | ATG | CTT | GCA | GAG |
| E | E | R | A | N | T | I | E | A | Q | L | K | E | A | Q | M | L | A | E |
| | 460 * | | | 470 * | | | 480 * | | | | 490 * | | | 500 * | | | 510 * | |
| GAA | GCC | GAC | CGA | AAA | TAC | GAT | GAG | GTC | GCC | CGT | AAA | TTG | GCC | ATG | GTT | GAA | GCT | GAT |
| E | A | D | R | K | Y | D | E | V | A | R | K | L | A | M | V | E | A | D |
| | | 520 * | | | 530 * | | | 540 * | | | | 550 * | | | 560 * | | | 570 * |
| CTT | GAA | AGG | GCC | GAA | GAA | CGT | GCT | GAA | GCC | GGA | GAG | AAC | AAG | ATC | GTC | GAA | TTG | GAA |
| L | E | R | A | E | E | R | A | E | A | G | E | N | K | I | V | E | L | E |
| | | | 580 * | | | 590 * | | | 600 * | | | | 610 * | | | 620 * | | |
| GAG | GAA | TTG | CGT | GTC | GTC | GGA | AAT | AAC | CTG | AAA | TCA | CTC | GAA | GTG | TCC | GAA | GAA | AAG |
| E | E | L | R | V | V | G | N | N | L | K | S | L | E | V | S | E | E | K |

TABLE 2-continued

DNA sequence of the Eco R1 cDNA fragment contained in plasmid pBTA 593 in clone BTA 1621 and the translated amino acid sequence coding for part of the 41kD protein of *T. colubriformis*.

| | | | | | | | | | | | | | | | | | | |
|---|---|---|---|---|---|---|---|---|---|---|---|---|---|---|---|---|---|---|
| 630 | | | | 640 | | | 650 | | | 660 | | | | 670 | | | 680 | |
| * | | | | * | | | * | | | * | | | | * | | | * | |
| GCA | CTG | CAA | CGT | GAG | GAC | TCA | TAC | GAA | GAG | CAG | ATT | CGT | ACC | ATT | TCA | TCT | CGT | CTG |
| A | L | Q | R | E | D | S | Y | E | E | Q | I | R | T | I | S | S | R | L |
| | 690 | | | | 700 | | | | | | | | | | | | | |
| | * | | | | * | | | | | | | | | | | | | |
| AAG | GAG | GCG | GAA | ACC | CGT | GCT | | | | | | | | | | | | |
| K | E | A | E | T | R | A | | | | | | | | | | | | |

The 700 bp insert was used to screen further cDNA libraries and clones were isolated which contained more of the coding and non coding regions of the *T. colubriformis* 41 kD gene. The DNA sequence of these clones was determined and the DNA sequence and translated amino acid sequence for the 41 kD gene is shown in Table 3.

TABLE 3

Sequence of *T. colubriformis* (41kD antigen)

| | | | | | | | | | | | | | | | | | |
|---|---|---|---|---|---|---|---|---|---|---|---|---|---|---|---|---|---|
| 1 | | | | | | | | | | 31 | | | | | | | |
| ATG | GAC | GCC | ATC | AAG | AAG | AAG | ATG | CAG | GCG | ATG | AAG | ATC | GAG | AAG | GAC | AAT | GCT |
| Met | Asp | Ala | Ile | Lys | Lys | Lys | Met | Gln | Ala | Met | Lys | Ile | Glu | Lys | Asp | Asn | Ala |
| | | 61 | | | | | | | | | | 91 | | | | | |
| CTC | GAT | CGA | GCC | GAT | GCC | GCC | GAA | GAG | AAA | GTC | CGT | CAA | ATT | ACC | GAA | AAG | TTG |
| Leu | Asp | Arg | Ala | Asp | Ala | Ala | Glu | Glu | Lys | Val | Arg | Gln | Ile | Thr | Glu | Lys | Leu |
| | | | 121 | | | | | | | | | | 151 | | | | |
| GAG | CGA | GTT | GAA | GAA | GAG | CTC | CGT | GAC | ACA | CAA | AAG | AAA | ATG | ATG | CAA | ACA | GAA |
| Glu | Arg | Val | Glu | Glu | Glu | Leu | Arg | Asp | Thr | Gly | Lys | Lys | Met | Met | Gln | Thr | Glu |
| | | | | | | 181 | | | | | | | | | | 211 | |
| AAC | GAT | TTG | GAC | AAG | GCT | CAG | GAA | GAT | TTG | GCT | GCA | GCC | ACC | AGC | CAG | TTG | GAA |
| Asn | Asp | Leu | Asp | Lys | Ala | Gln | Glu | Asp | Leu | Ala | Ala | Ala | Thr | Ser | Gln | Leu | Glu |
| | | | | | | | | 241 | | | | | | | | | |
| GAG | AAA | GAG | AAG | AAA | GTG | CAA | GAG | GCT | GAG | GCA | GAG | GTA | GCT | GCC | CTG | AAC | CGT |
| Glu | Lys | Glu | Lys | Lys | Val | Gln | Glu | Ala | Glu | Ala | Glu | Val | Ala | Ala | Leu | Asn | Arg |
| 271 | | | | | | | | | | 301 | | | | | | | |
| CGC | ATG | ACT | CTT | CTC | GAA | GAA | GAG | CTT | GAA | CGT | GCT | GAA | GAA | CGT | TTG | AAG | ATC |
| Arg | Met | Thr | Leu | Leu | Glu | Glu | Glu | Leu | Glu | Arg | Ala | Glu | Glu | Arg | Leu | Lys | Ile |
| | | 331 | | | | | | | | | | 361 | | | | | |
| GCC | ACT | GAA | AAA | CTC | GAA | GAG | GCC | ACT | CAC | AAT | GTC | GAC | GAG | TCC | GAG | CGT | GTA |
| Ala | Thr | Glu | Lys | Leu | Glu | Glu | Ala | Thr | His | Asn | Val | Asp | Glu | Ser | Glu | Arg | Val |
| | | | | 391 | | | | | | | | | | 421 | | | |
| CGC | AAA | GTG | ATG | GAG | AAC | GGC | TCA | TTC | CAA | GAT | GAG | GAG | CGT | GCC | AAC | ACG | ATT |
| Arg | Lys | Val | Met | Glu | Asn | Gly | Ser | Phe | Gln | Asp | Glu | Glu | Arg | Ala | Asn | Thr | Ile |
| | | | | | | 451 | | | | | | | | | | 481 | |
| GAA | GCT | CAA | CTG | AAG | GAA | GCC | CAG | ATG | CTT | GCA | GAG | GAA | GCC | GAC | CGA | AAA | TAC |
| Glu | Ala | Gln | Leu | Lys | Glu | Ala | Gln | Met | Leu | Ala | Glu | Glu | Ala | Asp | Arg | Lys | Tyr |
| | | | | | | | | 511 | | | | | | | | | |
| GAT | GAG | GTC | GCC | CGT | AAA | TTG | GCC | ATG | GTT | GAA | GCT | GAT | CTT | GAA | AGG | GCC | GAA |
| Asp | Glu | Val | Ala | Arg | Lys | Leu | Ala | Met | Val | Glu | Ala | Asp | Leu | Glu | Arg | Ala | Glu |
| 541 | | | | | | | | | | 571 | | | | | | | |
| GAA | CGT | GCT | GAA | GCC | GGA | GAG | AAC | AAG | ATC | GTC | GAA | TTG | GAA | GAG | GAA | TTG | CGT |
| Glu | Arg | Ala | Glu | Ala | Gly | Glu | Asn | Lys | Ile | Val | Glu | Leu | Glu | Glu | Glu | Leu | Arg |
| | | 601 | | | | | | | | | | 631 | | | | | |
| GTC | GTC | GGA | AAT | AAC | CTG | AAA | TCA | CTC | GAA | GTG | TCC | GAA | GAA | AAG | GCA | CTG | CAA |
| Val | Val | Gly | Asn | Asn | Leu | Lys | Ser | Leu | Glu | Val | Ser | Glu | Glu | Lys | Ala | Leu | Gln |
| | | | | 661 | | | | | | | | | | 691 | | | |
| CGT | GAG | GAC | TCA | TAC | GAA | GAG | CAG | ATT | CGT | ACC | ATT | TCA | TCT | CGT | CTG | AAG | GAG |
| Arg | Glu | Asp | Ser | Tyr | Glu | Glu | Gln | Ile | Arg | Thr | Ile | Ser | Ser | Arg | Leu | Lys | Glu |

TABLE 3-continued

| Sequence of *T. colubriformis* (41kD antigen) | | | | | | | | | | | | | | | | | |
|---|---|---|---|---|---|---|---|---|---|---|---|---|---|---|---|---|---|
| | | | | | 721 | | | | | | | | | | 751 | | |
| GCG | GAA | ACC | CGT | GCT | GAA | TTC | GCC | GAG | CGC | TCC | GTG | CAG | AAG | CTC | CAG | AAG | GAA |
| Ala | Glu | Thr | Arg | Ala | Glu | Phe | Ala | Glu | Arg | Ser | Val | Gln | Lys | Leu | Gln | Lys | Glu |
| | | | | | | | 781 | | | | | | | | | | |
| GTC | GAC | AGA | CTC | GAG | GAT | GAA | TTG | GTA | CAT | GAG | AAG | GAG | AGA | TAC | AAG | GCG | ATT |
| Val | Asp | Arg | Leu | Glu | Asp | Glu | Leu | Val | His | Glu | Lys | Glu | Arg | Tyr | Lys | Ala | Ile |
| 811 | | | | | | | | | 841 | | | | | | | | |
| TCC | GAG | GAG | CTT | GAC | TCG | ACC | TTC | CAA | GAA | CTC | TCC | GGC | TAT | | | | |
| Ser | Glu | Glu | Leu | Asp | Ser | Thr | Phe | Gln | Glu | Leu | Ser | Gly | Tyr | | | | |

Production of the 41 kD Protein as a Recombinant Fusion Protein with *E. coli* β-galactosidase IV. Subcloning the 700 bp 41 kD cDNA fragment into pUR290

A. Preparation of Fragment

DNA was prepared from clone lambdagtL4/41/6 according to Maniatis et al (1982). The DNA was cut with the restriction enzyme EcoR1 to release the 700 bp insert which was then purified for subsequent subcloning. Purification was carried out as follows: the EcoR1-cut DNA was separated by electrophoresis in an agarose gel and the 700 bp fragment collected on and eluted from NA45 paper according to the manufacturer's instructions (Schleicher & Schuell). The 700 bp DNA was then precipitated with isopropanol and redissolved in TE (10 mM Tris pH7.5-1 mM EDTA).

B. Cloning into pUR290

The expression vector pUR290 [Ruther and Muller-Hill, 1983] is a plasmid containing the bacterial β-galactosidase gene with a number of restriction enzyme sites near the 3' end into which foreign sequences can be inserted. The purified 700 bp cDNA fragment was ligated with EcoR1 digested pUR290 using methods described by Maniatis et al (1982). Coincidentally, the reading frame of the β-galactosidase gene at the EcoR1 restriction enzyme site is in phase with that of the 41 kD 700 bp cDNA fragment.

V. Detection of pUR Clones Producing Fusion Protein

The pUR clones expression 41 kD antigen were identified using serum from a rabbit which had been vaccinated with purified 41 kD protein. The colonies were grown on agar containing ampicillin and IPTG and replicas of the colonies were made on nitrocellulose. Those colonies expression 41 kD antigen were identified according to standard immunological screening methods [Maniatis et al (1982)] and probed with antisera-peroxidase method. A number of positive colonies were picked and grown in liquid culture for analysis on SDS-PAGE.

VI. Size of Fusion Protein on SDS-PAGE

The recombinant β-galactosidase/41 kD protein produced by strain BTA 1621 (which contains plasmid pBTA 593) is about 140 kD MW, of which approximately 27 kD is *T. colubriformis* in origin. Unfused β-galactosidase is about 120 kD MW (FIG. 3).

VII. Growth of BTA 1621 in Liquid Culture + IPTG

Recombinant clone BTA 1621, containing the 41 kD cDNA fragment inserted, in frame, at the 3' end of the bacterial β-galactosidase gene of pUR290 (plasmid pBTA 593), was grown in LB bacterial culture medium + ampicillin + IPTG at 21° overnight [Maniatis et al (1982)]. The bacteria were then collected and further processed for protein purification.

VIII. Purification of Fusion Protein for Animal Testing

For purification of the β-galactosidase/41 kD fusion protein, clone BTA 1621 was grown overnight in 500 ml LB+Amp(50 μg/ml)+IPTG)1 μg/ml) at 20° C. The bacteria were collected by centrifugation, treated with lysozyme (500 μg/ml in Tris EDTA buffer, 5' at 4°) and lysed by addition of NP40 to 1% v/v. Deoxyribonuclease was added to 100 μg/ml. Mg $Cl_2$ to 50 mM and the lysate incubated at 4° overnight. The lysate was then centrifuged at 10,000 rpm in a Beckman JA20 rotor for 10 min. The pellet, containing most of the fusion protein, was dissolved in 8M urea/1% β-mercaptoethanol in 50 mM tris-HCl (PH8), 100 mM NaCl and then chromatographed on a Superose 6 column (1.6 cm×80 cm). Using SDS-PAGE, fractions containing the fusion protein were identified and then pooled. Western blots [Towbin H, et al] indicate a positive reaction between the rabbit anti 41 kD antibody and the purified protein (see FIG. 3).

EXAMPLE 4

Experimental animals were chosen as described previously (O'Donnell et al. 1985).

41 kD was purified from PBS-DOC extracts of third state larvae of *Trichostrongylus colubriformis,* separated by two dimensional SDS-PAGE and electroeluted. This material was used to vaccinate guinea pigs intraperitoneally (O'Donnell et al 1985). It can be seen (Table 4) that the purified 41 kD fraction gave substantial protection (ranging from 43–51%) against *T. colubriformis* challenge infection in guinea pigs following vaccination.

TABLE 4

Vaccination of guinea pigs with purified 41kD protein from *T. colubriformis.*

| | Experiment No. | | | |
|---|---|---|---|---|
| Worm counts | 1 | 2 | 3a | 3b |
| Controls | 671 ± 257 (n = 10) | 963 ± 206 (n = 10) | 1056 ± 353 (n = 10) | 1056 ± 353 (n = 10) |
| Vaccinates | 364 ± 159 (n = 8) | 549 ± 351 (n = 6) | 550 ± 148 (n = 5) | 513 ± 149 (n = 5) |
| % Protection | 46 | 43 | 48 | 51 |
| μg injected | 85 | 50 | 50 | 100 |

All animals were injected intraperitoneally with the *T. colubriformis* 41 kD protein isolated from third stage larvae. The animals were challenged with 2000 infective larvae 28 days later and killed for worm counts 13 days post challenge.

Protection of 43–51% was given by the 41 kD immunogenic fraction when eluted from a Laemmli gel. It is reasonable to expect that it may be more potent if prepared by non denaturing means.

This 41 kD fraction exists in all juvenile and adult stages as demonstrated by immunoblotting with rabbit antisera against material electro-eluted after SDS-PAGE. However, antibodies (IgA, IgG or IgM) against 41 kD protein could not be detected in sera from several naturally-infected guinea pigs and sheep nor in the mesenteric lymph from a sheep infected with *T. colubriformis* (as studied by the immunoblot technique).

Use of 41 kD Fusion Protein as a VACCINE

As shown in Table 5 intraperitoneal injection of the recombinant 41 kD fusion protein purified from BTA 1621 gave similar protection to that achieved by the original 41 kD protein extracted from *T. colubriformis* larvae.

TABLE 5

VACCINATION OF GUINEA PIGS WITH 41kD - FUSION PROTEIN DERIVED FROM CLONE BTA 1621 (Worm Numbers)

| | Controls | Vaccinates | % Protection |
|---|---|---|---|
| Mean | 1135 ± [263] (n = 12) | 416 ± [220] (n = 3) | 63% |

T-test significance < 0.001

Animals were vaccinated with 450 $\mu$g fusion protein per guinea pig, challenged with 2000 infective *T. colubriformis* larvae 21 days later. Animals were killed for worm counts 13 days post-challenge.

EXAMPLE 5

Isolation and Characterisation of a cDNA Clone Encoding the Haemonchus Contortus 41 kD Protein Polyadenylated mRNA was extracted from young adult *H. contortus* and a cDNA library was constructed in lambda gtll using the methods essentially as described in International Patent Application No. PCT/AU87/00401.

Approximately $3\times10^4$ recombinant bacteriophage were screened with DNA fragments isolated from a clone coding for the *T. colubriformis* 41 kD protein. Duplicate nitrocellulose filters were prepared as described by Maniatis 1982. The probe was labelled according to the method of Feinberg and Vogelstein 1984. Hybridisation conditions used were as described by Reed. Four positive clones were detected and purified.

One of the isolated clones, 41/4, contained approximately 1.38 Kb of *H. contortus* cDNA with an internal Eco RI site. Digestion of the DNA isolated from the clone with Eco RI produced cDNA fragments of approximately 900 and 480 bp.

DNA was prepared from clone 41/4 (Maniatis 1982) and digested with Eco RI under conditions leading to partial or complete digestion. The DNA was electrophoresed in agarose gels and the 480 bp, 900 bp and 1.38 Kb fragments were isolated using NA45 paper (Schleicher and Schuell). The 480 and 900 bp fragments were subcloned into a vector PBTA224 which is a derivative of pUR290 (Ruther and Miller-Hill 1982) from which the Eco RI site outside the β-galactosidase gene has been removed. The 1.38 Kb partial digest fragment was subcloned into pBTA 502 which is a derivative of pUC18 (Yamisch-Perron, Vieira and Messing (1985)). Three clones were isolated and will be described:

Clone BTA1637 contains plasmid pBTA597 which is the 480 bp fragment in pBTA 224: clone BTA 1638 contains plasmid pBTA598 which is the 900 bp fragment in pBTA 224: clone BTA 1684 contains plasmid pBTA702 which is the 1.38 Kb partial digest fragment in plasmid pBTA502 (host strain is JM109 in all cases).

A series of deletions of the 1.38 Kb fragment contained in pBTA702 were made by digesting samples of the DNA with BamHI and Pstl followed by digestion of the linearized DNA with econuclease III and mung bean nuclease, for various periods of time, and religating the reaction products. The DNA was then transformed into JM109 and ampicillin resistant colonies were picked. The plasmids were characterized and the DNA sequence of the inserts in a selection of those transformants was determined using the method of Sanger et al as adapted by Hattori and Sakaki (1986) for use with double stranded DNA templates. The complete sequence of the cDNA segment in pBTA702 (Table 6) shows extensive homology to the cloned *T. colubriformis* gene.

TABLE 6

Sequence of the cDNA insert in pBTA702.

| 10 | 20 | 30 | 40 | 50 | 60 | 70 |
|---|---|---|---|---|---|---|
| GATTCGGAGC | GGCCACAGAC | GAAAGCAGCT | CGGCGTTTTT | CGGTCGTCGC | TTCCCGTTTT | GTTTGATCTC |
| 80 | 90 | 100 | 110 | 120 | 130 | 140 |
| TTCGAGAGGA | GCAGAAGAGA | GCGGTGTGAG | CGACTGCCGC | CCTCACAATT | TGCTGACAGT | CGCGCGACTT |
| 150 | 160 | 170 | 180 | 190 | 200 | 210 |
| CCACAAGTGC | TTCCACATTT | CTTGCTTGTC | TCGCTACGGC | TACCGATTTG | TTCTAAAGTA | TCATTCACAT |
| 220 | 230 | 240 | 250 | 260 | 270 | 280 |
| CTGAATCCAC | TACTGCCATC | ATGTCGAAAG | TGAACAAAGA | AGGAGCTCAG | CAGACATCTC | TGCTCGATGT |
| 290 | 300 | 310 | 320 | 330 | 340 | 350 |
| CCTCAAGAAG | AAAATGCGCC | AAGCCCGCGA | AGAGGCTGAA | GCTGCAAAGG | ACGAAGCCGA | TGAAGTGCAA |
| 360 | 370 | 380 | 390 | 400 | 410 | 420 |
| CGACAGCTCG | AAGAGGAACG | TAAAAAGCGT | GAGGACGCTG | AAGCTGAAGT | GGCAGCATTG | AATCGCCGCA |
| 430 | 440 | 450 | 460 | 470 | 480 | 490 |
| TTGTATTGGT | TGAGGAGGAT | TTGGAACGTA | CTGAAGATCG | TCTGAAGATT | GCCACATCCA | AATTGGAAGA |
| 500 | 510 | 520 | 530 | 540 | 550 | 560 |
| GGCTTCGAAG | GCAGCCGATG | AGGCTGAACG | AGCTCGAAGA | TCGTTGGAAA | ATCGTGTCGA | TGTCGATGAG |

TABLE 6-continued

Sequence of the cDNA insert in pBTA702.

| | | | | | | |
|---|---|---|---|---|---|---|
| 570 | 580 | 590 | 600 | 610 | 620 | 620 |
| GATCGTTGTG | CCGAGCTCGA | AACGAAACTA | CGTGAAGCTC | AAGCTCTTCT | GCATGAAACA | GAGAGTAAGA |
| 640 | 650 | 660 | 670 | 680 | 690 | 700 |
| GCGAAGAGGT | CGCCCGTAAG | CTGGCTATGG | TTGAAGCTGA | TCTCGAAAGA | GCCGAAGAAC | GTGCTGAAGC |
| 710 | 720 | 730 | 740 | 750 | 760 | 770 |
| CGGAGAGAAC | AAGATCGTCG | AGTTGGAAGA | GGAACTTCGT | GTCGTCGGAA | ACAACTTGAA | GTCACTTGAG |
| 780 | 790 | 800 | 810 | 820 | 830 | 840 |
| GTGTCTGAAG | AAAAGGCCCT | TCAACGTGAA | GACTCATACG | AGGAACAGAT | TCGTACTATC | TCAGCTCGTC |
| 850 | 860 | 870 | 880 | 890 | 900 | 910 |
| TGAAGGAGGC | GGAAACCCGT | GCCGAATTCG | CTGAGCGTTC | CGTGCAGAAA | CTCCAGAAGG | AAGTCGACAG |
| 920 | 930 | 940 | 950 | 960 | 970 | 980 |
| ACTGGAGGAT | GAATTGGTAC | ATGAGAAGGA | GAGATACAAG | GCAATTTCCG | AGGAGCTTGA | CTCGACCTTC |
| 990 | 1000 | 1010 | 1020 | 1030 | 1040 | 1050 |
| CAAGAACTGT | CCGGCTATTG | ATTTCTTCAT | TTTTTCCATC | AATCCATCCA | AATCATCCCC | GTCATTGCTG |
| 1060 | 1070 | 1080 | 1090 | 1100 | 1110 | 1120 |
| ACATTTTTTC | TACCGTACAT | GTGTCTCTTT | CCTTCTGTGC | TCCTGTTTCA | TCTATCATTC | GCAGTTTGTA |
| 1130 | 1140 | 1150 | 1160 | 1170 | 1180 | 1190 |
| GTCTACGCAA | TCACTCGAAC | GGTAATGCAT | CGCCTGAATA | TGTTCATAAT | CCCCCTCCGT | TTTAGCTTCT |
| 1200 | 1210 | 1220 | 1230 | 1240 | 1250 | 1260 |
| CATAGCACAT | TCGAGAAGCT | TCGCTTCACT | CTACCCAGTT | CTGTTTTACT | AACATCTATT | CGCGTCTTTT |
| 1270 | 1280 | 1290 | 1300 | 1310 | 1320 | 1330 |
| CACCTTCTTT | TTTGATGAAG | AGCAGGTCAA | AATAAAGAAT | TGAACGAAAA | AAAAAAAAAA | AAAAAAA |

From the DNA sequence, an open reading frame of 1032 base pairs can be identified which codes for a protein containing 344 amino acids (Table 6): The amino acid sequence corresponding to some of the peptide fragments generated by *A. Millea* digestion of the *T. colubriformis* antigen can be identified in the *H. contortus* cloned sequence (underlined in Table 7). The DNA sequence homology between the *H. contortus* and *T. colubriformis* clones is high over the region from amino acids 130 to 344. The N-terminal 130 amino acids however contain no such homology. Further analysis of the DNA sequence shows that the N-terminal segment of the *H. contortus* sequence is derived from DNA coding for 10 amino acids of 62-galactosidase followed by 77 irrelevant amino acids and a segment of 43 amino acids extending from a putative initiation codon. The DNA is fortuitously in phase and so gives rise to a 344 amino acid continuous open reading frame. In support of this proposal, the ATG which is presumed to be the initiating codon for the *H. contortus* antigen is preceded by a sequence TGCCATC which closely resembles the consensus sequence for a Shine-Dalgarno sequence in vertebrate genes vis agcCAcC.

TABLE 7

Sequence of the fusion protein produced by strain BTA 1684.

| | | | | | | | | | | | | | | | | | |
|---|---|---|---|---|---|---|---|---|---|---|---|---|---|---|---|---|---|
| 1 | | | | | | | | | | 31 | | | | | | | |
| ATG | ATT | ACG | AAT | TGC | CCG | GGA | GAT | CTG | GAA | TTC | CGA | TTC | GGA | GCG | GCC | ACA | GAC |
| Met | Ile | Thr | Asn | Cys | Pro | Gly | Asp | Leu | Glu | Phe | Arg | Phe | Gly | Ala | Ala | Thr | Asp |
| | | 61 | | | | | | | | | | 91 | | | | | |
| GAA | AGC | AGC | TCG | GCG | TTT | TTC | GGT | CGT | CGC | TTC | CCG | TTT | TGT | TTG | ATC | TCT | TCG |
| Glu | Ser | Ser | Ser | Ala | Phe | Phe | Gly | Arg | Arg | Phe | Pro | Phe | Cys | Leu | Ile | Ser | Ser |
| | | | | 121 | | | | | | | | | 151 | | | | |
| AGA | GGA | GCA | GAA | GAG | AGC | GGT | GTG | AGC | GAC | TGC | CGC | CCT | CAC | AAT | TTG | CTG | ACA |
| Arg | Gly | Ala | Glu | Glu | Ser | Gly | Val | Ser | Asp | Cys | Arg | Pro | His | Asn | Leu | Leu | Thr |
| | | | | | | 181 | | | | | | | | | | 211 | |
| GTC | GCG | CGA | CTT | CCA | CAA | GTG | CTT | CCA | CAT | TTC | TTG | CTT | GTC | TCG | CTA | CGG | CTA |
| Val | Ala | Arg | Leu | Pro | Gln | Val | Leu | Pro | His | Phe | Leu | Leu | Val | Ser | Leu | Arg | Leu |
| | | | | | | | | 241 | | | | | | | | | |
| CCG | ATT | TCT | TCT | AAA | GTA | TCA | TTC | ACA | TCT | GAA | TCC | ACT | ACT | GCC | ATC | ATG | TCG |
| Pro | Ile | Cys | Ser | Lys | Val | Ser | Phe | Thr | Ser | Glu | Ser | Thr | Thr | Ala | Ile | Met | Ser |
| 271 | | | | | | | | | | 301 | | | | | | | |
| AAA | GTG | AAC | AAA | GAA | GGA | GCT | CAG | CAG | ACA | TCT | CTG | CTC | GAT | GTC | CTC | AAG | AAG |
| Lys | Val | Asn | Lys | Glu | Gly | Ala | Gln | Gln | Thr | Ser | Leu | Leu | Asp | Val | Leu | Lys | Lys |

TABLE 7-continued

Sequence of the fusion protein produced by strain BTA 1684.

| | | | | | | | | | | | | | | | | | |
|---|---|---|---|---|---|---|---|---|---|---|---|---|---|---|---|---|---|
| | | 331 | | | | | | | | | | 361 | | | | | |
| AAA | ATG | CGC | CAA | GCC | CGC | GAA | GAG | GCT | GAA | GCT | GCA | AAG | GAC | GAA | GCC | GAT | GAA |
| Lys | Met | Arg | Gln | Ala | Arg | Glu | Glu | Ala | Glu | Ala | Ala | Lys | Asp | Glu | Ala | Asp | Glu |
| | | | | 391 | | | | | | | | | | 421 | | | |
| GTG | CAA | CGA | CAG | CTC | GAA | GAG | GAA | CGT | AAA | AAG | CGT | GAG | GAC | GCT | GAA | GCT | GAA |
| Val | Gln | Arg | Gln | Leu | Glu | Glu | Glu | Arg | Lys | Lys | Arg | Glu | Asp | Ala | Glu | Ala | Glu |
| | | | | | | 451 | | | | | | | | | | 481 | |
| GTG | GCA | GCA | TTG | AAT | CGC | CGC | ATT | GTA | TTG | GTT | GAG | GAG | GAT | TTG | GAA | CGT | ACT |
| Val | Ala | Ala | Leu | Asn | Arg | Arg | Ile | Val | Leu | Val | Glu | Glu | Asp | Leu | Glu | Arg | Thr |
| | | | | | | | | 511 | | | | | | | | | |
| GAA | GAT | CGT | CTG | AAG | ATT | GCC | ACA | TCC | AAA | TTG | GAA | GAG | GCT | TCG | AAG | GCA | GCC |
| Glu | Asp | Arg | Leu | Lys | Ile | Ala | Thr | Ser | Lys | Leu | Glu | Glu | Ala | Ser | Lys | Ala | Ala |
| 541 | | | | | | | | | | 571 | | | | | | | |
| GAT | GAG | GCT | GAA | CGA | GCT | CGA | AGA | TCG | TTG | GAA | AAT | CGT | GTC | GAT | GTC | GAT | GAG |
| Asp | Glu | Ala | Glu | Arg | Ala | Arg | Arg | Ser | Leu | Glu | Asn | Arg | Val | Asp | Val | Asp | Glu |
| | | 601 | | | | | | | | | | 631 | | | | | |
| GAT | CGT | TGT | GCC | GAG | CTC | GAA | ACG | AAA | CTA | CGT | GAA | GCT | CAA | GCT | CTT | CTG | CAT |
| Asp | Arg | Cys | Ala | Glu | Leu | Glu | Thr | Lys | Leu | Arg | Glu | Ala | Gln | Ala | Leu | Leu | His |
| | | | | 661 | | | | | | | | | | 691 | | | |
| GAA | ACA | GAG | AGT | AAG | AGC | GAA | GAG | GTC | GCC | CGT | AAG | CTG | GCT | ATG | GTT | GAA | GCT |
| Glu | Thr | Glu | Ser | Lys | Ser | Glu | Glu | Val | Ala | Arg | Lys | Leu | Ala | Met | Val | Glu | Ala |
| | | | | | | 721 | | | | | | | | | | 751 | |
| GAT | CTC | GAA | AGA | GCC | GAA | GAA | CGT | GCT | GAA | GCC | GGA | GAG | AAC | AAG | ATC | GTC | GAG |
| Asp | Leu | Glu | Arg | Ala | Glu | Glu | Arg | Ala | Glu | Ala | Gly | Glu | Asn | Lys | Ile | Val | Glu |
| | | | | | | | | 781 | | | | | | | | | |
| TTG | GAA | GAG | GAA | CTT | CGT | GTC | GTC | GGA | AAC | AAC | TTG | AAG | TCA | CTT | GAG | GTG | TCT |
| Leu | Glu | Glu | Glu | Leu | Arg | Val | Val | Gly | Asn | Asn | Leu | Lys | Ser | Leu | Glu | Val | Ser |
| 811 | | | | | | | | | | 841 | | | | | | | |
| GAA | GAA | AAG | GCC | CTT | CAA | CGT | GAA | GAC | TCA | TAC | GAG | GAA | CAG | ATT | CGT | ACT | ATC |
| Glu | Glu | Lys | Ala | Leu | Gln | Arg | Glu | Asp | Ser | Tyr | Glu | Glu | Gln | Ile | Arg | Thr | Ile |
| | | 871 | | | | | | | | | | 901 | | | | | |
| TCA | GCT | CGT | CTG | AAG | GAG | GCG | GAA | ACC | CGT | GCC | GAA | TTC | GCT | GAG | CGT | TCC | GTG |
| Ser | Ala | Arg | Leu | Lys | Glu | Ala | Glu | Thr | Arg | Ala | Glu | Phe | Ala | Glu | Arg | Ser | Val |
| | | | | 931 | | | | | | | | | | 961 | | | |
| CAG | AAA | CTC | CAG | AAG | GAA | GTC | GAC | AGA | CTG | GAG | GAT | GAA | TTG | GTA | CAT | GAG | AAG |
| Gln | Lys | Leu | Gln | Lys | Glu | Val | Asp | Arg | Leu | Glu | Asp | Glu | Leu | Val | His | Glu | Lys |
| | | | | | | 991 | | | | | | | | | | 1021 | |
| GAG | AGA | TAC | AAG | GCA | ATT | TCC | GAG | GAG | CTT | GAC | TCG | ACC | TTC | CAA | GAA | CTG | TCC |
| Glu | Arg | Tyr | Lys | Ala | Ile | Ser | Glu | Glu | Leu | Asp | Ser | Thr | Phe | Gln | Glu | Leu | Ser |
| GGC | TAT | | | | | | | | | | | | | | | | |
| Gly | Tyr | | | | | | | | | | | | | | | | |

Recombinant organisms have been constructed which lack the irrelevant N-terminal 87 amino acids. In order to produce a near native *H. contortus* antigen for vaccination studies. DNA from pBTA702 was digested with restriction enzymes Sma I and Asu II in combination and the 3514 and 613 as fragments were purified. The 513 bp fragment was then digested with DdeI and the 238 bp fragment was purified. This 238 bp fragment was then ligated to the 3514 bp fragment, the non-cohesive end was rendered blunt by treatment with the Klenow fragment of DNA polymerase I and the DNA was then ligated to form circles and used to transform *E. coli* strain JM109. Ampicillin resistant colonies were selected, the plasmid DNA was isolated and the DNA sequence was confirmed by restriction enzyme analysis. The DNA in plasmid pBTA 704 (strain BTA 1686) codes for a molecule of 252 amino acids (Table 8) which is only 4 amino acids shorter than mature *H. contortus* antigen. The 6 amino acids on the N-terminus are derived from β-galactosidase and the initiating methionine is preceded by the β-galactosidase Shine-Dalgarno sequence.

TABLE 8

Sequence of the fusion protein by strain BTA 1686.

| | | | | | | | | | | | | | | | | | |
|---|---|---|---|---|---|---|---|---|---|---|---|---|---|---|---|---|---|
| 1 | | | | | | | | | | 31 | | | | | | | |
| ATG | ATT | ACG | AAT | TGC | CCG | CAG | ACA | TCT | CTG | CTC | GAT | GTC | CTC | AAG | AAG | AAA | ATG |
| Met | Ile | Thr | Asn | Cys | Pro | Gln | Thr | Ser | Leu | Leu | Asp | Val | Leu | Lys | Lys | Lys | Met |
| | | 61 | | | | | | | | | | 91 | | | | | |
| CGC | CAA | GCC | CGC | GAA | GAG | GCT | GAA | GCT | GCA | AAG | GAC | GAA | GCC | GAT | GAA | GTG | CAA |
| Arg | Gln | Ala | Arg | Glu | Glu | Ala | Glu | Ala | Ala | Lys | Asp | Glu | Ala | Asp | Glu | Val | Gln |
| | | | | 121 | | | | | | | | | | 151 | | | |
| CGA | CAG | CTC | GAA | GAG | GAA | CGT | AAA | AAG | CGT | GAG | GAC | GCT | GAA | GCT | GAA | GTG | GCA |
| Arg | Gln | Leu | Glu | Glu | Glu | Arg | Lys | Lys | Arg | Glu | Asp | Ala | Glu | Ala | Glu | Val | Ala |
| | | | | | | 181 | | | | | | | | | | 211 | |
| GCA | TTG | AAT | CGC | CGC | ATT | GTA | TTG | GTT | GAG | GAG | GAT | TTG | GAA | CGT | ACT | GAA | GAT |
| Ala | Leu | Asn | Arg | Arg | Ile | Val | Leu | Val | Glu | Glu | Asp | Leu | Glu | Arg | Thr | Glu | Asp |
| | | | | | | | | 241 | | | | | | | | | |
| CGT | CTG | AAG | ATT | GCC | ACA | TCC | AAA | TTG | GAA | GAG | GCT | TCG | AAG | GCA | GCC | GAT | GAG |
| Arg | Leu | Lys | Ile | Ala | Thr | Ser | Lys | Leu | Glu | Glu | Ala | Ser | Lys | Ala | Ala | Asp | Glu |
| 271 | | | | | | | | | | 301 | | | | | | | |
| GCT | GAA | CGA | GCT | CGA | AGA | TCG | TTG | GAA | AAT | CGT | GTC | GAT | GTC | GAT | GAG | GAT | CGT |
| Ala | Glu | Arg | Ala | Arg | Arg | Ser | Leu | Glu | Asn | Arg | Val | Asp | Val | Asp | Glu | Asp | Arg |
| | | 331 | | | | | | | | | | 361 | | | | | |
| TGT | GCC | GAG | CTC | GAA | ACG | AAA | CTA | CGT | GAA | GCT | CAA | GCT | CTT | CTG | CAT | GAA | ACA |
| Cys | Ala | Glu | Leu | Glu | Thr | Lys | Leu | Arg | Glu | Ala | Gln | Ala | Leu | Leu | His | Glu | Thr |
| | | | | 391 | | | | | | | | | | 421 | | | |
| GAG | AGT | AAG | AGC | GAA | GAG | GTC | GCC | CGT | AAG | CTG | GCT | ATG | GTT | GAA | GCT | GAT | CTC |
| Glu | Ser | Lys | Ser | Glu | Glu | Val | Ala | Arg | Lys | Leu | Ala | Met | Val | Glu | Ala | Asp | Leu |
| | | | | | | 451 | | | | | | | | | | 481 | |
| GAA | AGA | GCC | GAA | GAA | CGT | GCT | GAA | GCC | GGA | GAG | AAC | AAG | ATC | GTC | GAG | TTG | GAA |
| Glu | Arg | Ala | Glu | Glu | Arg | Ala | Glu | Ala | Gly | Glu | Asn | Lys | Ile | Val | Glu | Leu | Glu |
| | | | | | | | | 511 | | | | | | | | | |
| GAG | GAA | CTT | CGT | GTC | GTC | GGA | AAC | AAC | TTG | AAG | TCA | CTT | GAG | GTG | TCT | GAA | GAA |
| Glu | Glu | Leu | Arg | Val | Val | Gly | Asn | Asn | Leu | Lys | Ser | Leu | Glu | Val | Ser | Glu | Glu |
| 541 | | | | | | | | | | 571 | | | | | | | |
| AAG | GCC | CTT | CAA | CGT | GAA | GAC | TCA | TAC | GAG | GAA | CAG | ATT | CGT | ACT | ATC | TCA | GCT |
| Lys | Ala | Leu | Gln | Arg | Glu | Asp | Ser | Tyr | Glu | Glu | Gln | Ile | Arg | Thr | Ile | Ser | Ala |
| | | 601 | | | | | | | | | | 631 | | | | | |
| CGT | CTG | AAG | GAG | GCG | GAA | ACC | CGT | GCC | GAA | TTC | GCT | GAG | CGT | TCC | GTG | CAG | AAA |
| Arg | Leu | Lys | Glu | Ala | Glu | Thr | Arg | Ala | Glu | Phe | Ala | Glu | Arg | Ser | Val | Gln | Lys |
| | | | | 661 | | | | | | | | | | 691 | | | |
| CTC | CAG | AAG | GAA | GTC | GAC | AGA | CTG | GAG | GAT | GAA | TTG | GTA | CAT | GAG | AAG | GAG | AGA |
| Leu | Gln | Lys | Glu | Val | Asp | Arg | Leu | Glu | Asp | Glu | Leu | Val | His | Glu | Lys | Glu | Arg |
| | | | | | | 721 | | | | | | | | | | 751 | |
| TAC | AAG | GCA | ATT | TCC | GAG | GAG | CTT | GAC | TCG | ACC | TTC | CAA | GAA | CTG | TCC | GGC | TAT |
| Tyr | Lys | Ala | Ile | Ser | Glu | Glu | Leu | Asp | Ser | Thr | Phe | Gln | Glu | Leu | Ser | Gly | Tyr |

EXAMPLE 6

Expression of *H. Contortus* Antigen by Recombinant Organisms

Recombinant *E. coli* strains BTA 1637, BTA 1638, BTA 1684 and BTA 1686 were grown in TSB containing ampicillin (50 μg/ml) until an OD of approximately 1. Isopropylthiogalactopyranoside (IPTG) was then added to a final concentration of 10 mM and the incubation was continued for a further 8–16 h. The cells were collected by centrifugation, lysed by sonication and the sonicate was centrifuged at 13,000×g for 10 min. The pellet and the supernatants were subjected to SDS-PAGE analysis (Laemmli 1970) and immunoblotting using antisera raised in rabbits against the *T. colubriformis* 41 kD antigen. Immune complexes were detected using $^{126}$I-protein A or goat-anti-rabbit antibodies conjugated to alkaline phosphatase. The fusion proteins were found mainly in the pellets of the cell lysates in the form of inclusion bodies. BTA 1637 produced a fusion of approximately 120 kd which was detected on both Coomassie stained gels and the protein blots. BTA 1638 produced a fusion protein of approximately 148 kd which could be detected on a protein blot but not readily on a Coomassie-blue stained gel. BTA 1684 and BTA1686 produced proteins of approximately 44 kd and 30 kd respectively which were readily visualized on both stained gels and protein blots. The molecular weight of each product was approximately that predicted from analysis of the DNA sequence in all cases.

To produce material for animal trials, BTA 1684 was inoculated into a fermenter containing minimal media and auxotrophic requirements and fermented until the OD reached 15.5 IPTG was added to a final concentration of 1 mM, a tryptone yeast extract enriched media was added and a glucose feed begun. 154 hours post inoculation the cells were collected by centrifugation, resuspended and lysed by four passages through a french press at 9,000 psi. The lysate was centrifuged at approximately and the pellet was resuspended in 8M urea, 100 mM DTT, 20 mM tris-HCI pH8.0. Following centrifugation, the supernatant was passed over a DEAE sepharose column which was resolved with a 0–1M gradient of NaCl. Fractions containing the fusion protein were pooled and desalted on a Sephacryl S-400 HR column in 1M acetic acid. The fractions containing the fusion protein were again pooled, bound to a Vydak $C_4$ column in 0.1% Trifluoroacetic acid (TFA) which was resolved with a linear gradient of 30%–45% acetonitrile. Fractions containing the fusion protein were pooled and exchanged into 1M acetic acid for storage. An aliquot of the purified material was taken and the N-terminal amino acid sequence determined using an Applied Biosystems amino acid analyser. The first 20 amino acids were as predicted vis Met Ile Thr Asn X Pro Gly Asp Leu Glu Phe X Phe Gly Ala Ala Thr Asp Glu Ser. The amino acid analysis and SDS PAGE analysis would indicate the recombinant product to be at least 85% pure.

EXAMPLE 7

Vaccination/Challenge Trials

A group 10 sheep reared worm free were vaccinated with the recombinant antigen purified from strain BTA 1684 described in Example 6. Each animal received two vaccinations subcutaneously. The first vaccination contained approximately 1 mg of protein emulsified in Freunds complete adjuvant and the second 28 days later contained approximately 250 μg emulsified in Freunds incomplete adjuvant. Two additional groups of ten animals were used, the first as infection controls received no vaccinations and the second as adjuvant controls received adjuvant alone. Sixty three days after the first vaccination, all animals were infected per os with 15,000 infective L3 larvae of *H. contortus*. Faecal samples were taken on days 22, 28, 36, 42, 50, 56 and 63 post challenge and eggs per g. faeces were determined. In addition, haematocrit values were assayed on days 37, 56 and 6 3post infection. All animals were slaughtered on day 63 and the number of adult *H. contortus* in the abomasum was counted. The results (Tables 9, 10 and 11) show that vaccination with the recombinant antigen had given significant protection to the sheet against parasitism.

Throughout the period of the experiment the vaccinated group had a reduced egg count compared to the control groups: approximately 25% over the first 4 time points and approximately 60% over the last 3 time points, average overall of 40% reduced egg counts. At all three time points where the haematocrit values were measured the vaccinated group were higher and therefore the animals were less distressed. At slaughter the vaccinated group contained fewer worms, on average 52% lower than the control groups.

This experiment confirms that an immune response raised against the recombinant 41 kD protein was capable of reducing egg production and worm burden of infected sheep by greater than 50% and this correlated with reduced blood loss in these animals.

NOTE: Two animals had to be removed from the trial for ethical reasons when their haematocrit values dropped below an arbitrarily chosen value of 15. One of these animals came from the challenge control group and was slaughtered on day 52 (faecal egg count (day 50) 168,000 worm burden 6440). The second, from the vaccinate group, was slaughtered on day 34 (faecal egg count (day 28) 62,400, worm burden 6775). The data for these animals has not been included in Tables 9–11. As can be seen from analysis of the data in Table 9, the major effect of vaccination was that of an accelerated expulsion of the parasites. The effects of vaccination on days 22–42 were very minor on the whole group so it is not surprising that some animals were poorly protected during this early period of time.

It is to be understood that as the vaccination regime is optimised, the degree of protection obtained would be expected to increase to such an extent that a highly effective vaccine based on this antigen could be developed.

TABLE 9

FAECAL EGG COUNTS

| Days Post Challenge | Challenge Controls (n = 9) | Adjuvant Controls (n = 10) | Vaccinates (n = 9) | Average % Protection |
|---|---|---|---|---|
| 22 | 3,311 ± 2,541 | 1,505 ± 2,019 | 1,611 ± 1,389 | 33% |
| 28 | 15,078 ± 10,566 | 17,740 ± 10,559 | 13,311 ± 8,704 | 20% |
| 34 | 50,467 ± 28,004 | 54,230 ± 30,102 | 45,400 ± 32,702 | 13% |
| 42 | 32,906 ± 19,439 | 27,405 ± 18,028 | 22,094 ± 14,003 | 27% |
| 50 | 40,289 ± 31,353 | 30,620 ± 19,911 | 14,439 ± 12,436 | 59% |
| 56 | 19,894 ± 20,383 | 23,535 ± 16,969 | 7,850 ± 9,614 | 64% |
| 63 | 29,417 ± 23,922 | 41,385 ± 50,019 | 13,817 ± 13,888 | 61% |
| | | | | = 40% |

TABLE 10

PACKED CELL VOLUMES

| DAYS POST CHALLENGE | CHALLENGE CONTROLS (n = 9) | ADJUVANT CONTROLS (n = 10) | VACCINATES (n = 9) |
|---|---|---|---|
| 37 | 22.4 ± 4.3 | 22.8 ± 4.6 | 24.2 ± 3.6 |
| 56 | 22.0 ± 4.3 | 24.9 ± 5.2 | 26.7 ± 3.0 |
| 63 | 24.6 ± 4.8 | 25.3 ± 4.8 | 27.6 ± 3.9 |

TABLE 11

| WORM COUNTS AT SLAUGHTER | | | | |
|---|---|---|---|---|
| CHALLENGE CONTROLS (n = 9) | ADJUVANT CONTROLS (n = 10) | VACCINATES (n = 9) | AVERAGE % PROTECTION | T. Test SIGNIFICANCE |
| 3700 ± 2243 | 3776 ± 3196 | 1804 ± 1146 | 52% | <0.20 |

EXAMPLE 8

Cross Species Protection by 41 Kd Cloned Antigen 2 groups of 6 guinea pigs were vaccinated with the recombinant antigen purified from strain BTA 1684 as described in Example 6. Each group received one vaccination intraperitoneally. One group received 100 $\mu$g of protein in buffer and the second group received 100 $\mu$g of protein emulsified in incomplete Freunds adjuvant. One additional group of 4 animals, infection controls received no vaccination. 28 days after the vaccination, all animals were infected per os with 2000 infective $L_3$ larvae of *T. colubriformis.* 14 days later, all animals were slaughtered and the number of worms were counted. The results (Table 12) show that vaccination with the antigen alone gave 31% protection while vaccination with the antigen in incomplete Freunds adjuvant gave 46% protection.

These figures are similar to the protection provided by the native 41 kD antigens isolated from *T. colubriformis* (Example 4).

TABLE 12

| | | Worm count | Protection | T-test Significance |
|---|---|---|---|---|
| Controls | (n = 4) | 1237 ± 142 | | |
| 44kD alone | (n = 5) | 853 ± 302 | 31% | <0.050 |
| 44kD in IFA | (n = 5) | 667 ± 195 | 46% | <0.005 |

These results demonstrate that the *H. contortus* 41 kD antigen is capable of giving significant cross species protection to animals against infection with *T. colubriformis.* By extension it is likely that similar cross species protection could be afforded against parasitism by a range of other species of parasitic nematodes by vaccination with the recombinant antigens described herein or by vaccination with recombinant antigens derived from the other species of parasitic nematodes using the technology described in this work.

It is anticipated that the degree of protection afforded to the host animal would be increased substantially to provide an effective vaccine following optimization of the antigen purification, formulation and vaccination procedures.

INDUSTRIAL APPLICATIONS

The current invention provides a description of a protein and the DNA sequence coding for that protein which can be used as an effective vaccine for protection against parasitism of animals by *Trichostrongylus colubriformis* and *Haemonchus contortus.*

Furthermore it has been demonstrated that antibodies raised against the purified protein isolated from *Trichostrongylus colubriformis* and the DNA sequences coding for this protein can be used to identify the related polypeptide and gene coding for that polypeptide from species of parasitic nematode other than *Trichostrongylus colubriformis.* Thus it is claimed that the same DNA sequence and antibodies can be used to identify related proteins and genes coding for those proteins in a range of other species of nematode which are parasitic to man and domestic animals and that these proteins will provide effective vaccines against parasitism by those species of nematode whether isolated from the parasite itself or produced by recombinant DNA technology. Species of parasites and hosts they may infect include for example.

*Trichinella spiralis* or *Ancylostoma caninum* infections of man, *Strongylus vulgaris* infections of horses, *Trichostrongylus colubriformis* infections of sheep, *Haemonchus contortus* infections of goats, *Ostertagia ostertagi* infections of cattle, *Ascaris suum* or *Trichinella spiralis* infections of pigs, *Toxascaris leonia* or *Uncinaria stenocephala* infections of cats and *Ancylostoma caninum* or *Trichuris vulpis* infections of dogs as well as infections of the circulatory system of man by larvae of *Texocara spp* infection by *Necator americanus, Ancylostoma duodenale, Ascaris lumbricoides, Trichuris trichiura, Enterobius vermicularus, Strongyloides stercorals* or *Wuchereria bancrofti* and of the circulatory system of dogs by *Dirofilaria immitis* as well as infections of the circulatory system, urogenital system, respiratory system, skin and succutaneous tissues of these and other species of animal. It should be noted that this list is by no means complete.

REFERENCES

Adams, D B and Cobon, G S 1984 in Reviews in Rural Science vol. 6 (Leng et al eds) National Library of Australia pp 67–74.

Benton, W D and R W, Davis, 1977, Science, 196, 180–182.

Dineen et al 1977 Int. J. Parasitol, 7, 211–215.

Dineen J K and Wagland B M (1982)—Immunoregulation of parasites in natural host-parasite systems—with special reference to the gastro-intestinal nematodes of sheep. In "Biology and Control of Endoparasites" (Eds. L E A Symons, A D Donald and J K Dineen), Academic Press, pp 297–323.

Dineen J K (1984)—Immunological control of helminthiasis by genetic manipulation of host and parasite. In "Immunogenetic approaches to the control of endoparasites" (Eds J K Dineen and P M Outteridge), CSIRO, Australia, pp 2–8.

Feinberg, A P and Vogelstein, B 1984, Anal. Biochem. 137, 266–267.

Hattori, M and Sakaki, Y. (1986) Anal. Biochem 152, 232–238.

Howe J G and Hershey J W B (1981)—A sensitive immunoblotting method for measuring protein synthesis initiation factor levels in lysates of *Escherichia coli—J of Biological Chemistry* 256, 12836–12839.

Huynh, T V, R A, Young and R W, Davis, pp 49–78 in DNA cloning Vol. 1 1985 ed D M, Glover.

Johnson et al, 1984, Gene Anal. Tech. 1, 3–8.

Kohler P (1986)—Progress in molecular parasitology—Experientia 42, 377–386.

Laemmli, U K, 1970, Nature, 227, 680–684.

Laemmli U K (1970)—Cleavage of structural proteins during the assembly of the head of bacteriophage T4—*Nature (London)* 227, 680–684.

McKern N M, O'Donnell I J, Stewart D J and Clark B L (1985)—Primary structure of pilin protein from *Bacteroides nodosus* strain 216: comparison with corresponding protein from strain 196. J General Microbiology 131, 1–6.

Maniatis T, Fritsch E F and Sambrook J (1982) Molecular Cloning: A Laboratory Manual (Cold Spring Harbour Laboratory).

Maruyama, T, T Gojobori, S-I, Aota and T Idemura, 1986, Nucleic Acids Research, 14, Supplement r151–r197.

May R B (1985)—Evolution of pesticide resistance—*Nature (London)* 315, 12–13.

Munn, E and Greenwood, B 1987, Parasitology.

Neilson, J T M, 1975, Int. J. Parasitol. 5, 427–430.

Neilson and Van de Walle, 1987 Vet. Parasitol. 211–221.

O'Donnell I J (1973)—A search for a simple keratin—fractionation and peptide mapping of proteins from feature keratins. *Aust. J. Biol. Sci.* 26, 401–13.

O'Donnell I J, Dineen J K, Rothwell T L W and Marshall R C (1985)—Attempts to probe the antigens and protective immunogens of *Trichostrongylus colubriformis* in immunoblots with sera from infected and hyperimmune sheep and high- and low-responder guinea pigs—*International Journal for Parasitology* 15, 129–136.

Payne J W (1973)—Polymerization of proteins with glutaraldehyde—*Biochem. J* 135, 867–873.

Racusen D (1979)—Glycoprotein detection in polyacrylamide gel with thyml and sulphuric acid—*Analytical Biochemistry* 99, 474–476.

Reed, K C. BIO-RAD Bulletin 1321.

Rothwell T L W (1978)—Vaccination against the nematode *Trichostrongylus colubriformis*—III. Some observations on factors influencing immunity to infection in vaccinated guinea-pigs-*International Journal for Parasitology* 8, 33–37.

Rothwell T L W and Griffiths D A (1977)—Comparison of the kinetics of expulsion of *Trichostrongylus colubriformis* from previously uninfected, reinfected, and vaccinated guinea pigs. J of Parasitology 63, 761–762.

Rothwell T L W and Love R L (1974)—Vaccination against the nematode *Trichostrongylus colubriformis*—I Vaccination of guinea-pigs with worm homogenates and soluble products released during in vitro maintenance—*International Journal for Parasitology* 4, 293–299.

Rubin R W and Leonardi C L (1983)—Two-dimensional polyarylamide gel electrophoresis of membrane proteins. In 'Methods in Enzymology' (Eds Sidney and Betta Fleischer) 96, 184–192.

Ruther U & Muller-Hill B (1983) EMBO J 1, 1217.

Sanger, F, Coulson, A R, Barrell, B G, Smith, A J H and Roe, B A 1980, J. Mol. Biol. 143, 161–178.

Silverstein D S and Despommier D D (1985)—Effect on *Trichinella spiralis* of host responses to purified antigens—*Science* 227, 948–950.

Stearne P A, van Driel I R, Grego B, Simpson R J and Goding J W (1985)—The murine plasma cell antigen PC-1: Purification and partial amino acid sequence. J of Immunology 134, 443–448.

Towbin H, Staenelin T and Gordon J (1979) PNAS 76(9), 4350–4354.

Wallace, R B, P F, Johnson, S Taneka, M Schold, K Itakura and J Abelson, 1985 Science 209, 1396–1400.

Yanisch-Perron, C., Vieira, J. and Messing. J. (1985) Gene 33, 103–119

We claim:

1. An isolated and purified DNA molecule encoding a parasitic nematode tropomyosin protein capable of conferring protective immunity against infection of a host by a parasitic nematode species, wherein said tropomyosin protein binds to antibodies raised against a protein isolated from *Trichostrongylus colubriformis,* wherein said *Trichostrongylus colubriformis* protein has an approximate molecular weight of 41 kD as determined by SDS-PAGE, and comprises the amino acid sequence:

Lys Lys Lys Met Gln Ala Met Lys Ile Glu Lys Asp Asn Ala Leu
Asp Arg Ala Asp Ala Ala Glu Glu Lys Val Arg Gln Ile Tru Glu Lys
Leu Glu Arg Val Glu Glu Glu Leu Arg Asp Thr Gln Lys Lys Met Met
Gln Thr Glu Asn Asp Leu Asp Lys Ala Gln Glu Asp Leu Ala Ala Ala
Thr Ser Gln Leu Glu Glu Lys Glu Lys Lys Val Gln Glu Ala Glu Ala
Glu Val Ala Ala Leu Asn Arg Arg Met Thr Leu Leu Glu Glu Glu Leu
Glu Arg Ala Glu Glu Arg Leu Lys Ile Ala Tru Glu Lys Leu Glu Glu
Ala Thr His Asn Val Asp Glu Ser Glu Arg Val Arg Lys Val Met Glu
Asn Gly Ser Phe Gln Asp Glu Glu Arg Ala Asn Thr Ile Glu Ala Gln
Leu Lys Glu Ala Gln Met Leu Ala Glu Glu Ala Asp Arg Lys Tyr Asp
Glu Val Ala Arg Lys Leu Ala Met Val Glu Ala Asp Leu Glu Arg Ala
Glu Glu Arg Ala Glu Ala Gly Glu Asn Lys Ile Val Glu Leu Glu Glu
Glu Leu Arg Val Val Gly Asn Asn Leu Lys Ser Leu Glu Val Ser Glu
Glu Lys Ala Leu Gln Arg Glu Asp Ser Tyr Glu Glu Gln Ile Arg Thr
Ile Ser Ser Arg Leu Lys Glu Ala Glu Thr Arg Ala.

2. A DNA molecule according to claim 1, wherein said parasitic nematode species is selected from the group consisting of *Trichinella spiralis, Ancylostoma caninum, Strongylus vulgaris, Ostertagia ostertagi, Ascaris suum, Trichinella spiralis, Toxascaris leonia, Uncinaria stenocephalia, Ancylostoma caninum, Trichuris vulpis, Dirofilaria immitis,* a larva of Toxocara spp, *Trichostrongylus colubriformis, Haemonchus contortus, Necator americanus, Ancylostoma duodenale, Ascaris lumbricoides, Trichuris trichiura, Enterobius vermicularus, Strongyloides stercorals* or *Wuchereria bancrofti.*

3. A DNA molecule according to claim 1 wherein said nematode tropomyosin protein is derived from *T. colubriformis* or *H. contortus.*

4. A DNA molecule according to claim 1, wherein said DNA molecule encodes a protein comprising the sequence:

Lys Lys Lys Met Gln Ala Met Lys Ile Glu Lys Asp Asn Ala Leu
Asp Arg Ala Asp Ala Ala Glu Glu Lys Val Arg Gln Ile Tru Glu Lys
Leu Glu Arg Val Glu Glu Glu Leu Arg Asp Thr Gln Lys Lys Met Met
Gln Thr Glu Asn Asp Leu Asp Lys Ala Gln Glu Asp Leu Ala Ala Ala
Thr Ser Gln Leu Glu Glu Lys Glu Lys Lys Val Gln Glu Ala Glu Ala
Glu Val Ala Ala Leu Asn Arg Arg Met Thr Leu Leu Glu Glu Glu Leu
Glu Arg Ala Glu Glu Arg Leu Lys Ile Ala Tru Glu Lys Leu Glu Glu
Ala Thr His Asn Val Asp Glu Ser Glu Arg Val Arg Lys Val Met Glu
Asn Gly Ser Phe Gln Asp Glu Glu Arg Ala Asn Thr Ile Glu Ala Gln
Leu Lys Glu Ala Gln Met Leu Ala Glu Glu Ala Asp Arg Lys Tyr Asp
Glu Val Ala Arg Lys Leu Ala Met Val Glu Ala Asp Leu Glu Arg Ala
Glu Glu Arg Ala Glu Ala Gly Glu Asn Lys Ile Val Glu Leu Glu Glu
Glu Leu Arg Val Val Gly Asn Asn Leu Lys Ser Leu Glu Val Ser Glu
Glu Lys Ala Leu Gln Arg Glu Asp Ser Tyr Glu Glu Gln Ile Arg Thr
Ile Ser Ser Arg Leu Lys Glu Ala Glu Thr Arg Ala.

5. A DNA molecule according to claim 1, wherein said DNA molecule encodes a protein comprising the sequence:

Gln Thr Ser Leu Leu Asp Val Leu Lys Lys Lys Met Arg Gln Ala
Arg Glu Glu Ala Glu Ala Ala Lys Asp Glu Ala Asp Glu Val Gin Arg
Gln Leu Glu Glu Glu Arg Lys Lys Arg Glu Asp Ala Glu Ala Glu Val
Ala Ala Leu Asn Arg Arg Ile Val Leu Val Glu Glu Asp Leu Glu Arg
Thr Glu Asp Arg Leu Lys Ile Ala Thr Ser Lys Leu Glu Glu Ala Ser
Lys Ala Ala Asp Glu Ala Glu Arg Ala Arg Arg Ser Leu Glu Asn Arg
Val Asp Val Asp Glu Asp Arg Sys Ala Glu Leu Glu Thr Lys Leu Arg
Glu Ala Gln Ala Leu Leu His Glu Thr Glu Ser Lys Ser Glu Glu Val
Ala Arg Lys Leu Ala Met Val Glu Ala Asp Leu Glu Arg Ala Glu Glu
Arg Ala Glu Ala Gly Glu Asn Lys Ile Val Glu Leu Glu Glu Glu Leu
Arg Val Val Gly Asn Asn Leu Lys Ser Leu Glu Val Ser Glu Glu Lys
Ala Leu Gln Arg Glu Asp Ser Tyr Glu Glu Glu Ile Arg Thr Ile Ser
Ala Arg Leu Lys Glu Ala Glu Thr Arg Ala Glu Phe Ala Glu Arg Ser
Val Gln Lys Leu Gln Lys Glu Val Asp Arg Leu Glu Asp Glu Leu Val
His Glu Lys Glu Arg Tyr Lys Ala Ile Ser Glu Glu Leu Asp Ser Thr
Phe Gln Glu Leu Ser Gly Tyr.

6. A host cell transformed with a recombinant DNA molecule according to claim 1.

7. A host cell according to claim 6 wherein said host cell is selected from the group consisting of a bacteria cell, yeast, fungi other than yeast, a vertebrate cell or insect cell, plant cell, human cell, human tissue cell or whole eukaryotic organism.

8. A host cell according to claim 7 wherein said host cell is an enteric organism.

9. A host according to claim 8 wherein said host is *E. coli* K12 strain JM109 or Y1090.

10. A method for preparing a nematode tropomyosin protein capable of conferring protective immunity against infection of a host by a parasitic nematode species, said method comprising the steps of culturing a host cell according to claim 6 and then isolating said protein from said microorganism.

11. A method according to claim 10, wherein said tropomyosin protein is a fusion protein that also comprises a peptide sequence homologous to said host cell.

12. A method according to claim 10, wherein said host cell is selected from the group consisting of bacteria, yeast, fungi other than yeast, vertebrate and insect cells.

13. A method according to claim 12, wherein said host cell is a bacterial cell.

14. A method according to claim 13, wherein said host cell is *E. coli.*

15. A method according to claim 11, wherein said host cell is *E. coli,* and said peptide sequence homologous to said host cell is derived from *E. coli* β-galactosidase.

16. A DNA molecule according to claim 4, wherein the protein encoded by said DNA molecule further comprises the sequence:

Glu Phe Ala Glu Arg Ser Val Gln Lys Leu Gln Lys Glu Val Asp Arg Leu Glu Asp Glu Leu Val His Glu Lys Glu Arg Tyr Lys Ala Ile Ser Glu Glu Leu Asp Ser Thr Phe Gln Glu Leu Ser Gly Tyr.

17. An isolated and purified DNA molecule comprising the sequence:

AAG AAG AAG ATG CAG GCG ATG AAG ATC GAG AAG GAC AAT GCT CTC GAT
CGA GCC GAT GCC GCC GAA GAG AAA GTC CGT CAA ATT ACC GAA AAG TTG

-continued

GAG CGA GTT GAA GAA GAG CTC CGT GAC ACA CAA AAG AAA ATG ATG CAA

ACA GAA AAC GAT TTG GAC AAG GCT CAG GAA GAT TTG GCT GCA GCC ACC

AGC CAG TTG GAA GAG AAA GAG AAG AAA GTG CAA GAG GCT GAG GCA GAG

GTA GCT GCC CTG AAC CGT CGC ATG ACT CTT CTC GAA GAA GAG CTT GAA

CGT GCT GAA GAA CGT TTG AAG ATC GCC ACT GAA AAA CTC GAA GAG GCC

ACT CAC AAT GTC GAC GAG TCC GAG CGT GTA CGC AAA GTG ATG GAG AAC

GGC TCA TTC CAA GAT GAG GAG CGT GCC AAC ACG ATT GAA GCT CAA CTG

AAG GAA GCC CAG ATG CTT GCA GAG GAA GCC GAC CGA AAA TAC GAT GAG

GTC GCC CGT AAA TTG GCC ATG GTT GAA GCT GAT CTT GAA AGG GCC GAA

GAA CGT GCT GAA GCC GGA GAG AAC AAG ATC GTC GTA TTG GAA GAG GAA

TTG CGT GTC GTC GGA AAT AAC CTG AAA TCA CTC GAA GTG TCC GAA GAA

AAG GCA CTG CAA CGT GAG GAC TCA TAC GAA GAG CAG ATT CGT ACC ATT

TCA TCT CGT CTG AAG GAG GCG GAA ACC CGT GCT.

18. An isolated and purified DNA molecule comprising the sequence:

ATG GAC GCC ATC AAG AAG AAG ATG CAG GCG ATG AAG ATC GAG AAG GAC

AAT GCT CTC GAT CGA GCC GAT GCC GCC GAA GAG AAA GTC CGT CAA ATT

ACC GAA AAG TTG GAG CGA GTT GAA GAA GAG CTC CGT GAC ACA CAA AAG

AAA ATG ATG CAA ACA GAA AAC GAT TTG GAC AAG GCT CAG GAA GAT TTG

GCT GCA GCC ACC AGC CAG TTG GAA GAG AAA GAG AAG AAA GTG CAA GAG

GCT GAG GCA GAG GTA GCT GCC CTG AAC CGT CGC ATG ACT CTT CTC GAA

GAA GAG CTT GAA CGT GCT GAA CAA CGT TTG AAG ATC GCC ACT GAA AAA

CTC GAA GAG GCC ACT CAC AAT GTC GAC GAG TCC GAG CGT GTA CGC AAA

GTG ATG GAG AAC GGC TCA TTC CAA GAT GAG GAG CGT GCC AAC ACG ATT

GAA GCT CAA CTG AAG GAA GCC CAG ATG CTT GCA GAG GAA GCC GAC CGA

AAA TAC GAT GAG GTC GCC CGT AAA TTG GCC ATG GTT GAA GCT GAT CTT

GAA AGG GCC GAA GAA CGT GCT GAA GCC GGA GAG AAC AAG ATC GTC GAA

TTG GAA GAG GAA TTG CGT GTC GTC GGA AAT AAC CTG AAA TCA CTC GAA

-continued

GTG TCC CAA GAA AAG GCA CTG CAA CGT GAG GAC TCA TAC GAA GAG CAG

ATT CGT ACC ATT TCA TCT CGT CTG AAG GAG GCG GAA ACC CGT GCT GAA

TTC GCC GAG CGC TCC GTG CAG AAG CTC CAG AAG GAA GTC GAC AGA CTC

GAG GAT GAA TTG GTA CAT GAG AAG GAG AGA TAC AAG GCG ATT TCC GAG

GAG CTT GAC TCG ACC TTC CAA GAA CTC TCC GGC TAT.

19. An isolated and purified DNA molecule comprising the sequence:

GATTCGGAGC GGCCACAGAC GAAAGCAGCT CGGCGTTTTT CGGTCGTCGC

TTCCCGTTTT GTTTGATCTC TTCGAGAGGA GCAGAAGAGA GCGGTGTGAG

CGACTGCCGC CCTCACAATT TGCTGACAGT CGCGCGACTT CTACAAGTGC

TTCCACATTT CTTGCTTGTC TCGCTACGGC TACCGATTTG TTCTAAAGTA

TGATTGACAT CTGAATCCAC TACTGCCATC ATGTCGAAAG TGAACAAAGA

AGGAGCTCAG CAGACATCTC TGCTCGATGT CCTCAAGAAG AAAATGCGCC

AAGCCCGCGA AGAGGCTGAA GCTGCAAAGG ACGAAGCCGA TGAAGTGCAA

CGACAGCTCG AAGAGGAACG TAAAAAGCGT GAGGACGCTG AAGCTGAAGT

GGCAGCATTG AATCGCCGCA TTGTATTGGT TGAGGAGGAT TTGGAACGTA

CTGAAGATCG TCTGAAGATT CCCACATCCA AATTGGAAGA GGCTTCGAAG

GCAGCCGATG AGGCTGAACG AGCTCGAAGA TCGTTGGAAA ATCGTGTCGA

TGTCGATGAG GATCGTTGTG CCGAGCTCGA AACGAAACTA CGTGAAGCTC

AAGCTCTTCT GCATGAAACA GAGAGTAAGA GCGAAGAGGT CGCCCGTAAG

CTGGCTATGG TTGAAGCTGA TCTCGAAAGA GCCGAAGAAC CTGCTGAAGC

CGGAGAGAAC AAGATCGTCG AGTTGGAAGA GGAACTTCGT GTCGTCGGAA

ACAACTTGAA GTCACTTGAG GTGTCTGAAG AAAAGGCCCT TCAACGTGAA

GACTCATACG AGGAACAGAT TCGTACTATC TCAGCTCGTC TGAAGGAGGC

GGAAACCCGT GCCGAATTCG CTGAGCGTTC CGTGCAGAAA CTCCAGAAGG

AAGTCGACAG ACTGGAGGAT GAATTGGTAC ATGAGAAGGA GAGATACAAG

GCAATTTCCG AGGAGCTTGA CTCGACCTTC CAAGAACTGT CCGGCTATTG

ATTTCTTCAT TTTTTCCATC AATCCATCCA AATCATCCCC GTCATTGCTG

-continued

ACATTTTTC TACCGTACAT GTGTCTCTTT CCTTCTGTGC TCCTGTTTCA

TCTATCATTC GCAGTTTGTA GTCTACGCAA TCACTCGAAC GGTAATGCAT

CGCCTGAATA TGTTCATAAT CCCCCTCCGT TTTACTTTCT CATAGCACAT

TCGAGAAGCT TCGCTTCACT CTACCCAGTT CTGTTTTACT AACATCTATT

CGCGTCTTTT CACCTTCTTT TTTGATGAAG AGCAGGTCAA AATAAAGAAT

TGAACGAAAA AAAAAAAAAA AAAAAAA.

20. An isolated and purified DNA molecule comprising the sequence:

ATG ATT ACG AAT TGC CCG GGA GAT CTG GAA TTC CGA TTC GGA GCG GCC

ACA GAC GAA AGC AGC TCG GCG TTT TTC GGT CGT CGC TTC CCG TTT TGT

TTG ATC TCT TCG AGA GGA GCA GAA GAG AGC GGT GTG AGC GAC TGC CGC

CCT CAC AAT TTG CTG ACA GTC GCG CGA CTT CCA CAA GTG CTT CCA CAT

TTC TTG CTT GTC TCG CTA CGG CTA CCG ATT TGT TCT AAA GTA TCA TTC

ACA TCT GAA TCC ACT ACT GCC ATC ATG TCG AAA GTG AAC AAA GAA GGA

GCT CAG CAG ACA TCT CTG CTC GAT GTC CTC AAG AAG AAA ATG CGC CAA

GCC CGC GAA GAG GCT GAA GCT GCA AAG GAC GAA GCC GAT GAA GTG CAA

CGA CAG CTC GAA GAG GAA CGT AAA AAG CGT GAG GAC GCT GAA GCT GAA

GTG GCA GCA TTG AAT CGC CGC ATT GTA TTG GTT GAG GAG GAT TTG GAA

CGT ACT GAA GAT CGT CTG AAG ATT GCC ACA TCC AAA TTG GAA GAG GCT

TCG AAG GCA GCC GAT GAG GCT GAA CGA GCT CGA AGA TCG TTG GAA AAT

CGT GTC GAT GTC GAT GAG GAT CGT TGT GCC GAG CTC GAA ACG AAA CTA

CGT GAA GCT CAA GCT CTT CTG CAT GAA ACA GAG AGT AAG AGC GAA GAG

GTC GCC CGT AAG CTG GCT ATG GTT GAA GCT GAT CTC GAA AGA GCC GAA

GAA CGT GCT GAA GCC GGA GAG AAC AAG ATC GTC GAG TTG GAA GAG GAA

CTT CGT GTC GTC GGA AAC AAC TTG AAG TCA CTT GAG GTG TCT GAA GAA

AAG GCC CTT CAA CGT GAA GAC TCA TAC GAG GAA CAG ATT CGT ACT ATC

TCA GCT CGT CTG AAG GAG GCG GAA ACC CGT GCC GAA TTC GCT GAG CGT

TCC GTG CAG AAA CTC CAG AAG GAA GTC GAC AGA CTG GAG GAT GAA TTG

GTA CAT GAG AAG GAG AGA TAC AAG GCA ATT TCC GAG GAG CTT GAC TCG

ACC TTC CAA GAA CTG TCC GGC TAT.

21. An isolated and purified DNA molecule comprising the sequence:

ATG ATT ACG AAT TGC CCG CAG ACA TCT CTG CTC GAT GTC CTC AAG AAG

AAA ATG CGC CAA GCC CGC GAA GAG GCT GAA GCT GCA AAG GAC GAA GCC

GAT GAA GTG CAA CGA CAG CTC GAA GAG GAA CGT AAA AAG CGT GAG GAC

GCT GAA GCT GAA GTG GCA GCA TTG AAT CGC CGC ATT GTA TTG GTT GAG

GAG GAT TTG GAA CGT ACT GAA GAT CGT CTG AAG ATT GCC ACA TCC AAA

-continued

TTG GAA GAG GCT TCG AAG GCA GCC GAT GAG GCT GAA CGA GCT CGA AGA

TCG TTG GAA AAT CGT GTC GAT GTC GAT GAG GAT CGT TGT GCC GAG CTC

GAA ACG AAA CTA CGT GAA GCT CAA GCT CTT CTG CAT GAA ACA GAG AGT

AAG AGC GAA GAG GTC GCC CGT AAG CTG GCT ATG GTT GAA GCT GAT CTC

GAA AGA GCC GAA GAA CGT GCT GAA GCC GGA GAG AAC AAG ATC GTG GAG

TTG GAA GAG GAA CTT CGT GTC GTC GGA AAC AAC TTG AAG TCA CTT GAG

GTG TCT GAA GAA AAG GCC CTT CAA CGT GAA GAC TCA TAC GAG GAA CAG

ATT CGT ACT ATC TCA GCT CGT CTG AAG GAG GCG GAA ACC CGT GCC GAA

TTC GCT GAG CCT TCC GTG CAG AAA CTC CAG AAG GAA GTC GAC AGA CTG

GAG GAT GAA TTG GTA CAT GAG AAG GAG AGA TAC AAG GCA ATT TCC GAG

GAG CTT GAC TCG ACC TTC CAA GAA CTG TCC GGC TAT.

22. Plasmid pBTA593.

23. Plasmid pBTA597.

24. Plasmid pBTA598.

25. Plasmid pBTA702.

26. Plasmid pBTA704.

* * * * *